(12) United States Patent
Sato et al.

(10) Patent No.: US 10,729,313 B2
(45) Date of Patent: Aug. 4, 2020

(54) BEND INFORMATION COMPUTATION APPARATUS, ENDOSCOPE SYSTEM INCLUDING BEND INFORMATION COMPUTATION APPARATUS, BEND INFORMATION COMPUTATION METHOD, AND PROGRAM FOR BEND INFORMATION COMPUTATION

(71) Applicant: OLYMPUS CORPORATION, Tokyo (JP)

(72) Inventors: Ken Sato, Hachioji (JP); Yasuo Sasaki, Machida (JP); Hiromasa Fujita, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 374 days.

(21) Appl. No.: 15/800,199

(22) Filed: Nov. 1, 2017

(65) Prior Publication Data

US 2018/0055336 A1 Mar. 1, 2018

Related U.S. Application Data

(63) Continuation of application No. PCT/JP2015/063134, filed on May 1, 2015.

(51) Int. Cl.
*A61B 1/005* (2006.01)
*A61B 1/00* (2006.01)
(Continued)

(52) U.S. Cl.
CPC ........... *A61B 1/0052* (2013.01); *A61B 1/00* (2013.01); *A61B 1/0051* (2013.01); *A61B 1/01* (2013.01);
(Continued)

(58) Field of Classification Search
USPC .................................................. 385/32, 13
See application file for complete search history.

(56) References Cited

U.S. PATENT DOCUMENTS 5,321,257 A * 6/1994 Danisch ............ G02B 6/02066
250/227.16
5,840,024 A * 11/1998 Taniguchi ............ A61B 1/0051
600/424
(Continued)

FOREIGN PATENT DOCUMENTS

JP 2007-143600 A 6/2007
JP 2014-117446 A 6/2014
(Continued)

OTHER PUBLICATIONS

International Preliminary Report on Patentability together with the Written Opinion from related International Application No. PCT/JP2015/063134 dated Nov. 16, 2017.
(Continued)

*Primary Examiner* — Anh Tuan T Nguyen
*Assistant Examiner* — Shankar Raj Ghimire
(74) *Attorney, Agent, or Firm* — Scully, Scott, Murphy & Presser, P.C.

(57) ABSTRACT

A bend information computation apparatus is to compute bend information representing a direction and a magnitude of bend of a target group including targets disposed at an identical position along a light guide. Each target modulates the intensity of guided light in accordance with the direction and magnitude of bend. The apparatus includes an input unit to be input detected light quantity information corresponding to each target, a storage to store a bend coefficient and intensity modulation information of each target, and a light quantity information relationship between the bend coefficient and intensity modulation information and the detected light quantity information, a first arithmetic operator to
(Continued)

calculate light quantity variation information of each target, based on the detected light quantity information and light quantity information relationship, and a second arithmetic operator to calculate the bend information of the target group, based on the light quantity variation information and bend coefficient.

10 Claims, 22 Drawing Sheets

(51) Int. Cl.
    *A61B 5/06*     (2006.01)
    *A61B 34/20*     (2016.01)
    *A61B 1/01*     (2006.01)
    *A61B 1/07*     (2006.01)

(52) U.S. Cl.
    CPC ............... *A61B 1/07* (2013.01); *A61B 5/065* (2013.01); *A61B 34/20* (2016.02); *A61B 2034/2061* (2016.02)

(56) References Cited

U.S. PATENT DOCUMENTS

| | | | | |
|---|---|---|---|---|
| 6,127,672 A * | 10/2000 | Danisch | ................ | G01B 11/18 250/227.14 |
| 6,563,107 B2 * | 5/2003 | Danisch | ................ | G01B 11/18 250/227.14 |
| 6,846,286 B2 * | 1/2005 | Suzuki | ............... | A61B 1/00071 600/117 |
| 7,296,363 B2 * | 11/2007 | Danisch | ............... | G01P 15/125 33/556 |
| 7,440,661 B2 * | 10/2008 | Kobayashi | ............. | A61B 5/065 385/117 |
| 8,219,180 B2 * | 7/2012 | Cao | ........................ | A61B 5/06 600/117 |
| 8,248,413 B2 * | 8/2012 | Gattani | ................ | A61B 1/0005 345/419 |
| 8,248,414 B2 * | 8/2012 | Gattani | ............. | A61B 1/00009 345/424 |
| 8,737,777 B2 * | 5/2014 | Pitwon | .................. | G02B 6/125 385/32 |
| 8,780,339 B2 * | 7/2014 | Udd | ...................... | G01B 11/18 356/73.1 |
| 8,784,303 B2 * | 7/2014 | Laby | ................... | A61B 1/0052 600/117 |
| 9,138,166 B2 * | 9/2015 | Wong | .................... | A61B 5/065 |
| 9,784,569 B2 * | 10/2017 | Froggatt | ............. | G01M 11/025 |
| 2001/0056282 A1 * | 12/2001 | Sonnenschein | ...... | A61B 1/0005 606/139 |
| 2002/0088931 A1 * | 7/2002 | Danisch | ................. | G01D 5/268 250/227.14 |
| 2008/0192241 A1 * | 8/2008 | He | ...................... | G02B 6/2852 356/73.1 |
| 2008/0212082 A1 * | 9/2008 | Froggatt | ............. | G01M 11/083 356/73.1 |
| 2009/0208143 A1 * | 8/2009 | Yoon | ................... | A61B 1/0058 382/321 |
| 2010/0076263 A1 * | 3/2010 | Tanaka | ............... | A61B 1/00006 600/109 |
| 2013/0184553 A1 * | 7/2013 | Kassab | ............... | A61B 5/0538 600/381 |
| 2013/0345719 A1 * | 12/2013 | Donhowe | .......... | A61B 1/00167 606/130 |
| 2014/0054451 A1 * | 2/2014 | Abedin | .................. | G01L 1/243 250/227.14 |
| 2014/0257095 A1 * | 9/2014 | Kemp | ..................... | A61B 8/12 600/427 |
| 2016/0256228 A1 * | 9/2016 | Haartsen | ........... | A61M 25/0158 |

FOREIGN PATENT DOCUMENTS

| | | |
|---|---|---|
| JP | 2014-150868 A | 8/2014 |
| JP | 2014-188047 A | 10/2014 |
| JP | 2015-029831 A | 2/2015 |

OTHER PUBLICATIONS

Japanese Office Action dated Aug. 21, 2018 in Japanese Patent Application No. 2017-516243.
International Search Report dated Jul. 21, 2015 issued in PCT/JP2015/063134.

* cited by examiner

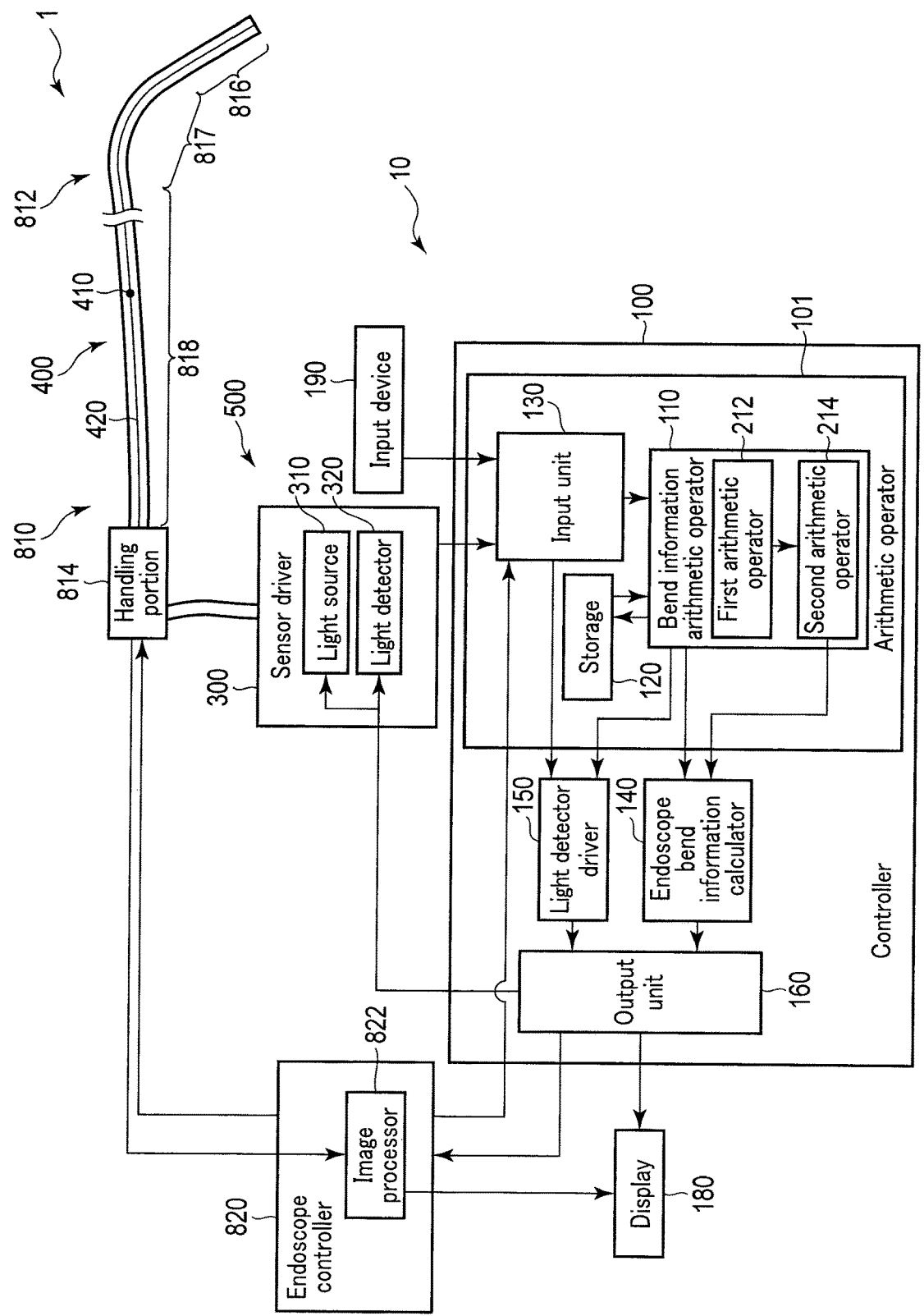
F I G. 1

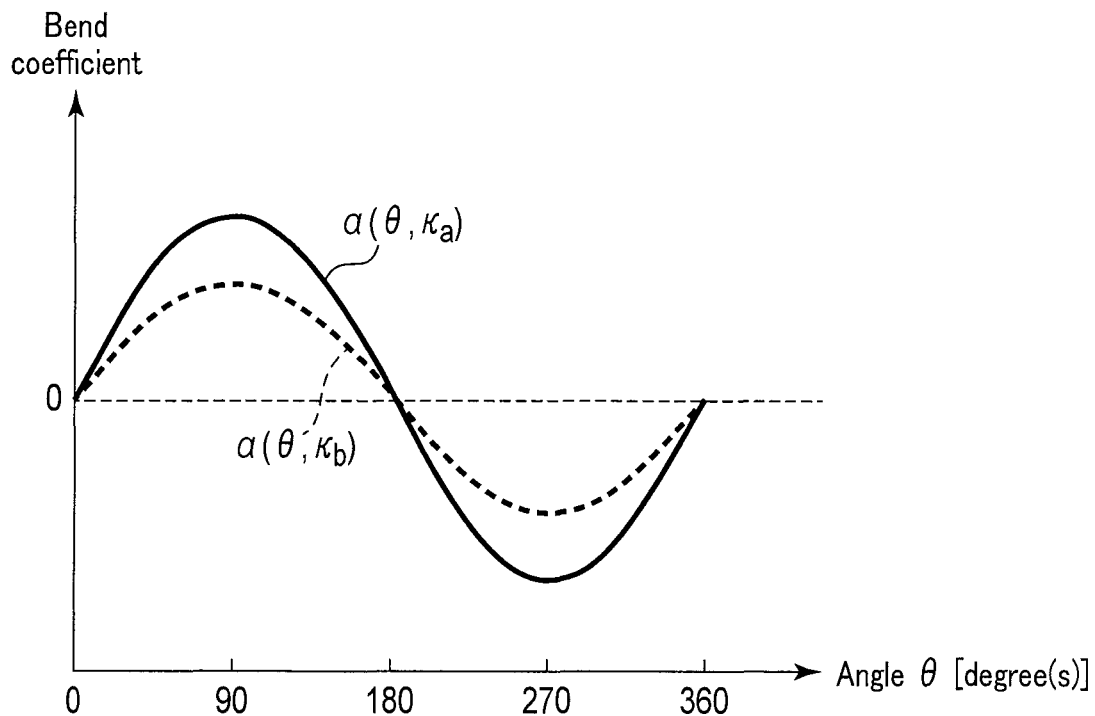
F I G. 11
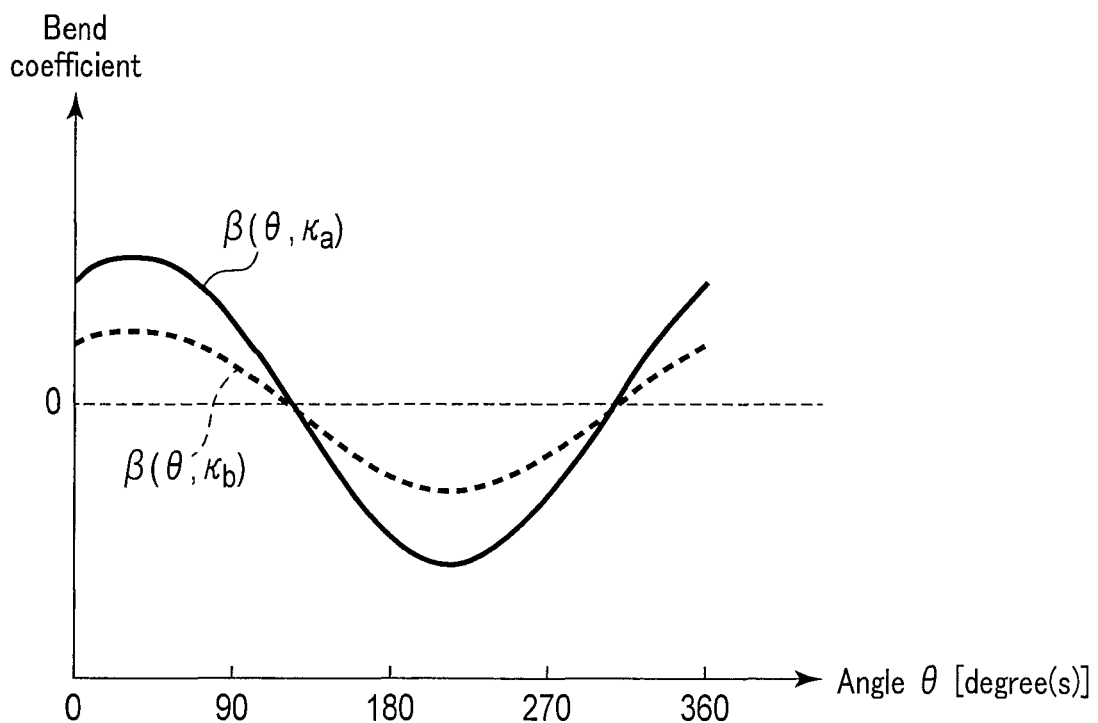
F I G. 12

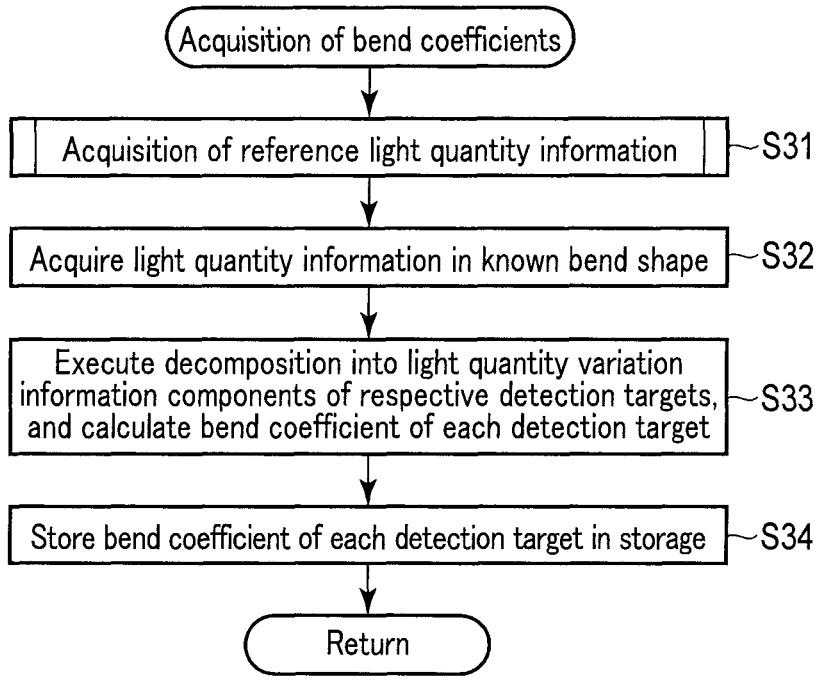
F I G. 16
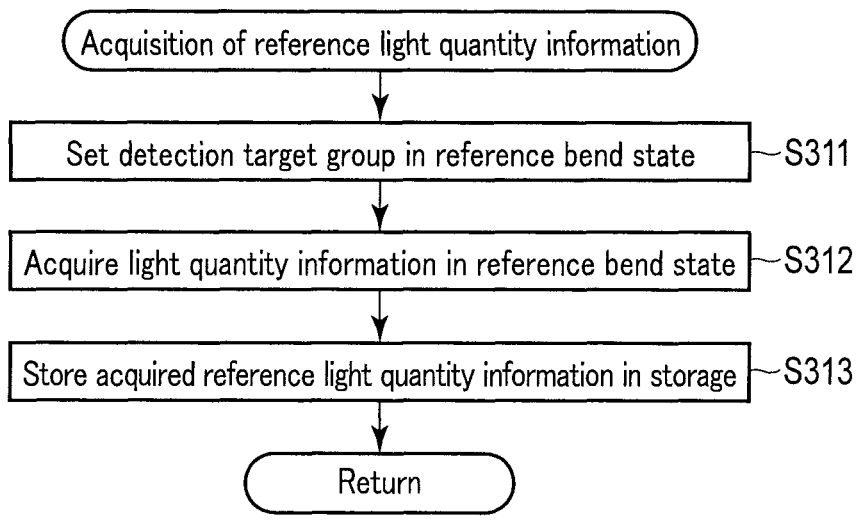
F I G. 17

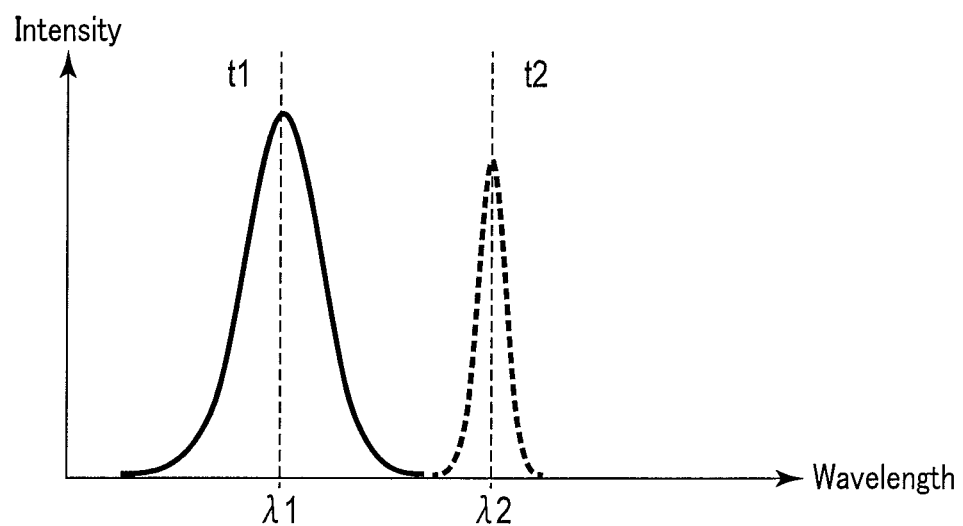
F I G. 22
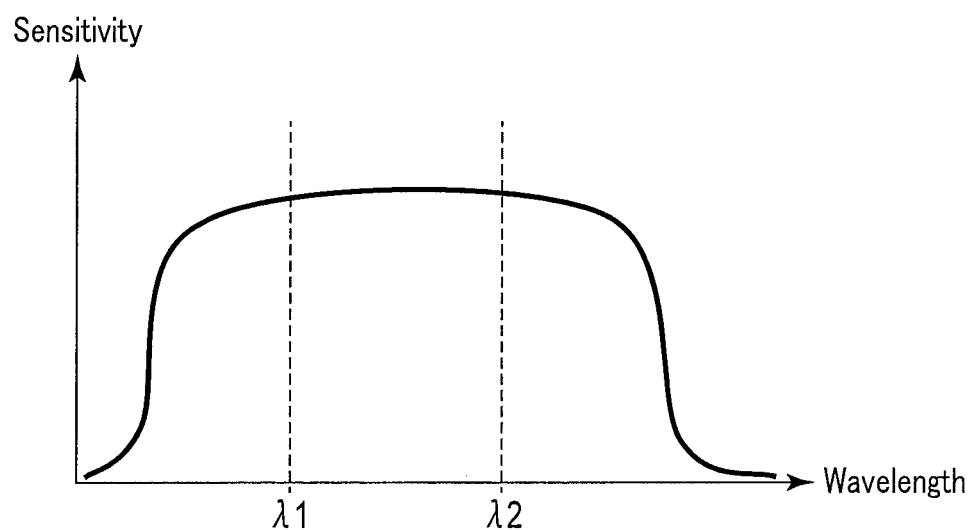
F I G. 23

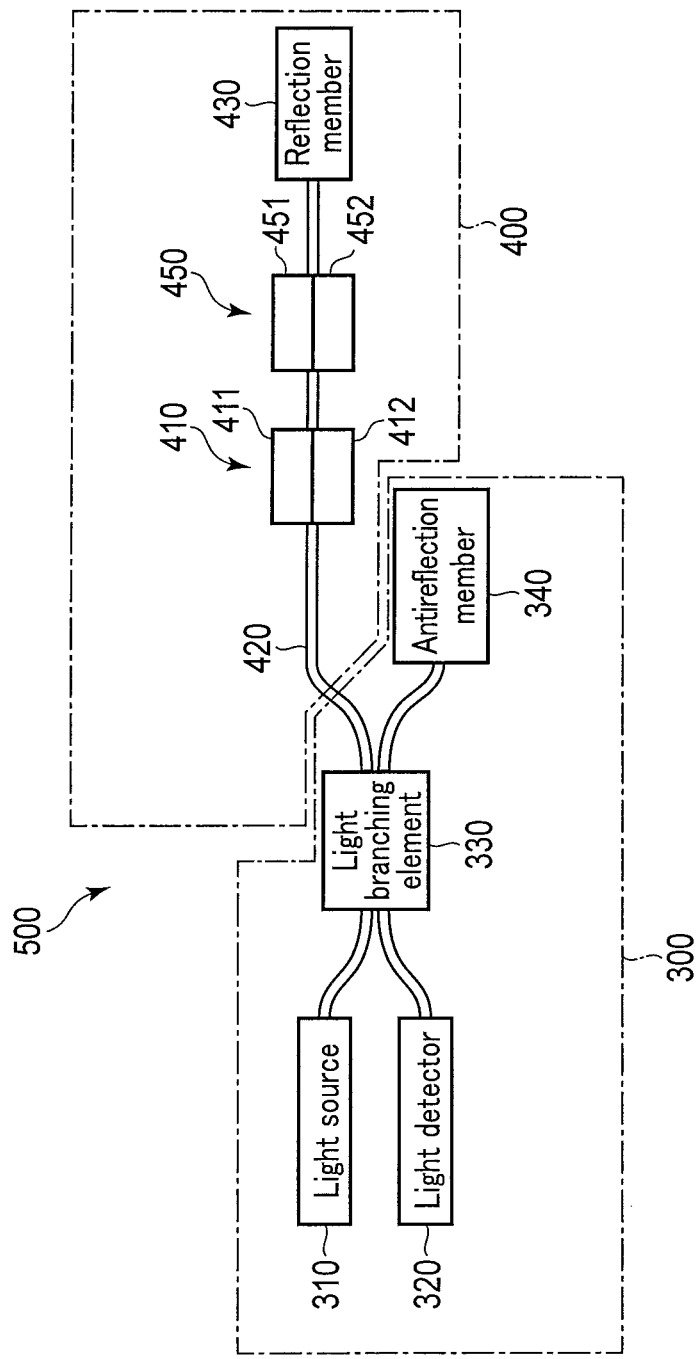
F I G. 26

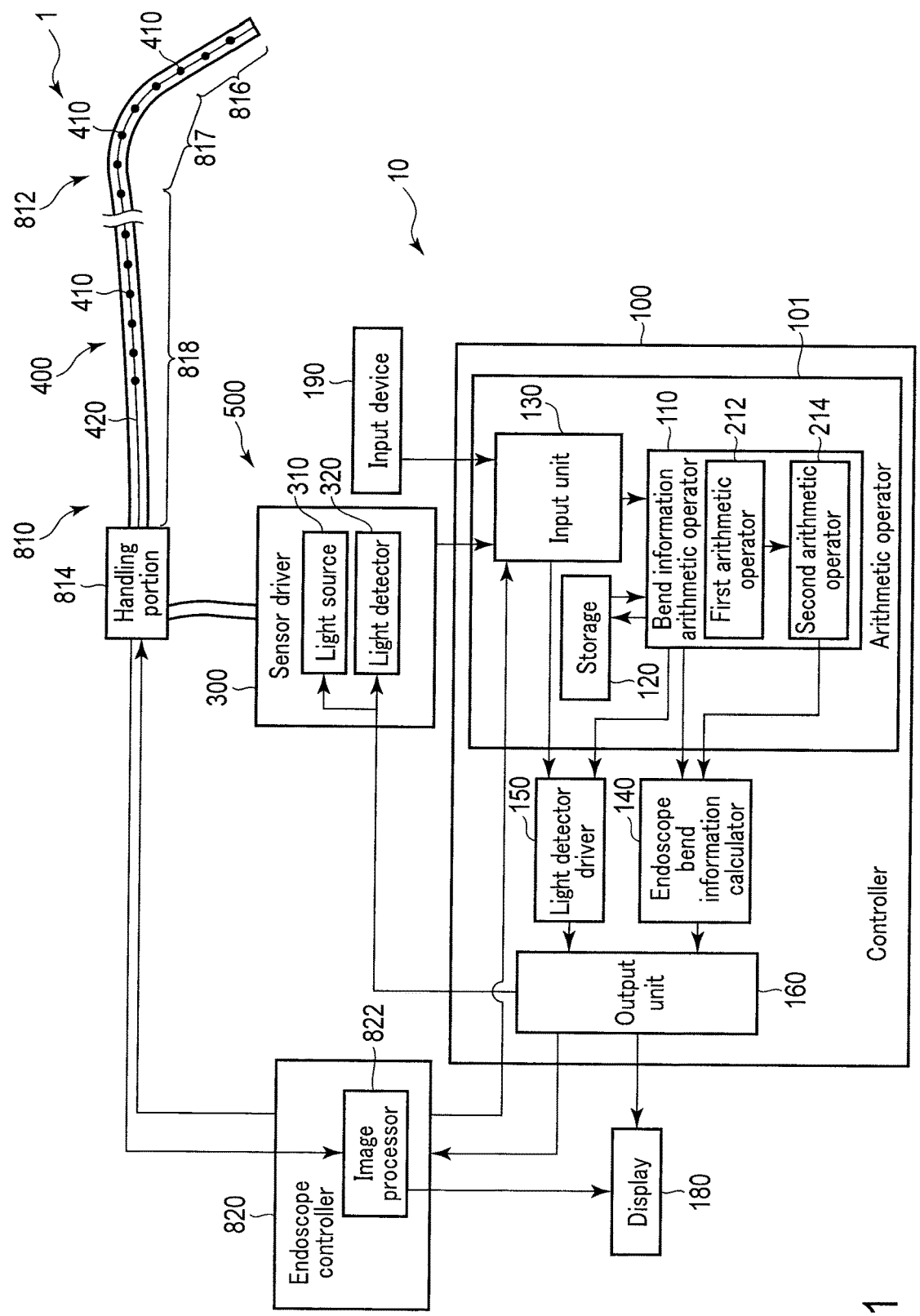
F I G. 31

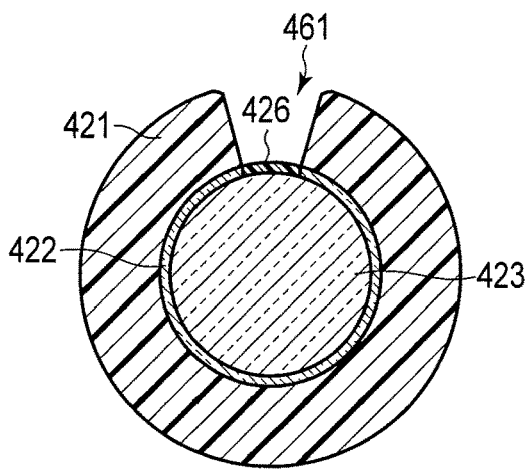
F I G. 32A
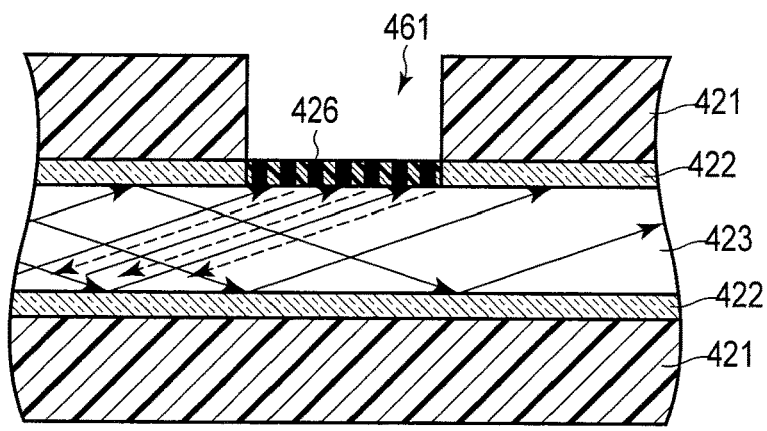
F I G. 32B
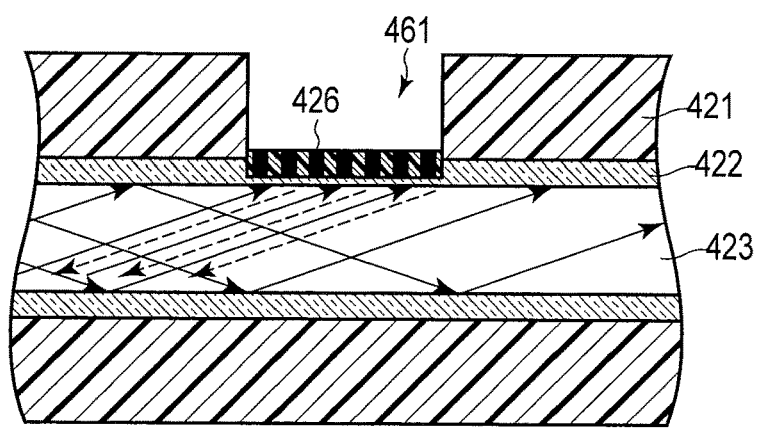
F I G. 33

BEND INFORMATION COMPUTATION APPARATUS, ENDOSCOPE SYSTEM INCLUDING BEND INFORMATION COMPUTATION APPARATUS, BEND INFORMATION COMPUTATION METHOD, AND PROGRAM FOR BEND INFORMATION COMPUTATION

CROSS REFERENCE TO RELATED APPLICATIONS

This application is a Continuation Application of PCT Application No. PCT/JP2015/063134, filed May 1, 2015, the entire contents of which are incorporated herein by reference.

BACKGROUND OF THE INVENTION

1. Field of the Invention

The present invention relates to a bend information computation apparatus to compute bend information representing a bend state of an object with flexibility, an endoscope system including the bend information computation apparatus, a bend information computation method, and a program for bend information computation.

2. Description of the Related Art

There is known a device, incorporated into a flexible insertion portion of an insertion apparatus (e.g. an endoscope), for detecting a bend state of the insertion portion. For example, Jpn. Pat. Appln. KOKAI Publication No. 2007-143600 discloses an endoscope shape detection probe employing an optical fiber. The detection probe includes the optical fiber that bends as one piece with an insertion portion of an endoscope. The optical fiber is provided with two optical modulators for detecting two-directional curvatures of, for example, an X direction and a Y direction, at a substantially identical position in the longitudinal direction of the optical fiber. The optical modulators modulate the intensity, etc. of wavelength components of light traveling through the optical fiber. The probe detects the curvature of the optical fiber at the optical modulators, accordingly the curvature of the insertion portion that bends as one piece with the optical fiber, is detected based on the intensity, etc. of wavelength components before and after passage through the optical modulators.

BRIEF SUMMARY OF THE INVENTION

An embodiment of the present invention is a bend information computation apparatus to compute bend information representing a direction of bend and a magnitude of bend of a detection target group provided on a light guide. The detection target group includes a plurality of detection targets disposed at an identical position along a length of the light guide. Each of the detection targets modulates the intensity of light guided by the light guide in accordance with the direction of bend and the magnitude of bend. The bend information computation apparatus includes an input unit to be input detected light quantity information of light of a wavelength corresponding to each of the detection targets, a storage to store a bend coefficient and intensity modulation information of each of the detection targets, and a light quantity information relationship representing a relationship between the bend coefficient and intensity modulation information and the detected light quantity information, a first arithmetic operator to calculate light quantity variation information of each of the detection targets, based on the detected light quantity information and the light quantity information relationship, and a second arithmetic operator to calculate the bend information of the detection target group, based on the light quantity variation information and the bend coefficient.

Another embodiment of the present invention is endoscope system including the aforementioned bend information computation apparatus, an endoscope provided with the light guide in an insertion portion, and an endoscope bend information calculator to calculate bend information of the insertion portion, based on the bend information.

Another embodiment of the present invention is a bend information computation method to compute bend information representing a direction of bend and a magnitude of bend of a detection target group provided on a light guide. The detection target group includes a plurality of detection targets disposed at an identical position along a length of the light guide. Each of the detection targets modulates the intensity of light guided by the light guide in accordance with the direction of bend and the magnitude of bend. The bend information computation method includes acquiring detected light quantity information of light of a wavelength corresponding to each of the detection targets, acquiring a bend coefficient and intensity modulation information of each of the detection targets, and a light quantity information relationship representing a relationship between the bend coefficient and intensity modulation information and the detected light quantity information, calculating light quantity variation information of each of the detection targets, based on the detected light quantity information and the light quantity information relationship, and calculating the bend information of the detection target group, based on the light quantity variation information and the bend coefficient.

Another embodiment of the present invention is a program for bend information computation to compute bend information representing a direction of bend and a magnitude of bend of a detection target group provided on a light guide. The detection target group includes a plurality of detection targets disposed at an identical position along a length of the light guide. Each of the detection targets modulates the intensity of light guided by the light guide in accordance with the direction of bend and the magnitude of bend. The program causes a computer to execute acquiring detected light quantity information of light of a wavelength corresponding to each of the detection targets, acquiring a bend coefficient and intensity modulation information of each of the detection targets, and a light quantity information relationship representing a relationship between the bend coefficient and intensity modulation information and the detected light quantity information, calculating light quantity variation information of each of the detection targets, based on the detected light quantity information and the light quantity information relationship, and calculating the bend information of the detection target group, based on the light quantity variation information and the bend coefficient.

Additional objects and advantages of the invention will beset forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute apart of the specification, illustrate embodiments of the invention, and together with the general description given above and the detailed description of the embodiments given below, serve to explain the principles of the invention.

FIG. 1 is a view schematically showing the configuration of an endoscope system including a bend information computation apparatus according to a first embodiment.

FIG. 11 is a graph showing an example of a bend coefficient obtained with respect to a first wavelength.

FIG. 12 is a graph showing an example of a bend coefficient obtained with respect to a second wavelength.

FIG. 16 is a flowchart showing an example of acquisition of bend coefficients.

FIG. 17 is a flowchart showing an example of acquisition of reference light quantity information.

FIG. 22 is a graph showing an example of the relationship between the wavelength and the light emission intensity of the light source at a certain time instant.

FIG. 23 is a graph showing an example of the relationship between the wavelength of light falling on the light detector and the detection sensitivity of the light detector, corresponding to FIG. 22.

FIG. 26 is a block diagram showing an example of the configuration of the sensor in a third embodiment.

FIG. 31 is a view schematically showing the configuration of an endoscope system including a bend information computation apparatus including a number of detection target groups.

FIG. 32A is a cross-sectional view in a radial direction of a light guide including another detection target alternative to the detection targets of the first to third embodiments.

FIG. 32B is a cross-sectional view including an optical axis of the light guide shown in FIG. 32A.

FIG. 33 is a cross-sectional view including an optical axis of a light guide including another detection target alternative to the detection target shown in FIG. 32A and FIG. 32B.

DETAILED DESCRIPTION OF THE INVENTION

First Embodiment

Figure 2:
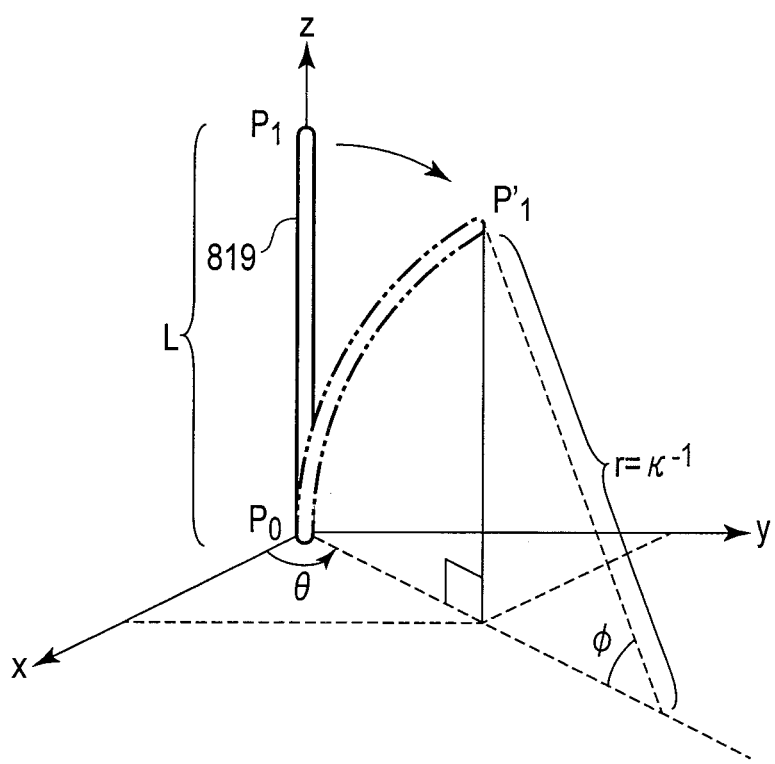
FIG. 2 is a view for explaining a quantity representing a state of bend of a flexible portion.

FIG. 1 is a view schematically showing the configuration of an endoscope system 1 including a bend information computation apparatus 10 (hereinafter referred to as "computation apparatus 10") according to a first embodiment of the present invention. The endoscope system 1 includes an endoscope 810, an endoscope controller 820, the computation apparatus 10, a display 180, and an input device 190.

The endoscope 810 includes an insertion portion 812, which is to be inserted into an insertion target, and a handling portion 814, which is coupled to a base end side of the insertion portion 812. The insertion portion 812 includes a hard end portion 816, a bendable portion 817 provided on a tip end side of the hard end portion 816, and a flexible tube 818 provided on a tip end side of the bendable portion 817. In the hard end portion 816, an illumination optical system, an observation optical system, an image sensor, etc., which are not shown, are incorporated. The bendable portion 817 is bent in a desired direction by operating the handling portion 814. The flexible tube 818 is free to bend. The handling portion 814 is used for various kinds of operations of the endoscope 810, including the above-described bending operation among others.

The endoscope controller 820 controls various operations of the endoscope 810. In addition, the endoscope controller 820 includes an image processor 822 for processing an image acquired by the observation optical system and the image sensor.

The computation apparatus 10 is a device for computing bend information presenting the bend state of the insertion portion 812, in particular, of the bendable portion 817 and flexible tube 818 (hereinafter these are referred to as "flexible portion 819").

The bend information will be explained with reference to FIG. 2. FIG. 2 shows, by a solid line, the flexible portion 819 with a length L, which is linearly positioned from an origin $P_0$ (0, 0, 0) to a point $P_1$ (0. 0, L). It is assumed that the flexible portion 819 has bent as indicated by an imaginary line in FIG. 2, and the point $P_1$ (0, 0, L) has shifted to a point $P'_1$ (x, y, z). Here, for the purpose of convenience, it is assumed that the flexible portion 819 is bent in an arcuate shape. At this time, in order to express the bend state of the flexible portion 819, two pieces of information, namely a direction of bend and a magnitude of bend, are necessary. The direction of bend is expressed by, for example, an angle θ formed between a straight line passing through a point (x, y, 0), at which the point $P'_1$ (x, y, z) is projected onto an xy plane, and the origin $P_0$ (0, 0, 0), and an x axis. In addition, the magnitude of bend is expressed by, for example, a curvature κ, a radius of curvature $r=κ^{-1}$, or a central angle φ=L/r=κL. In this manner, in the present specification, the direction of bend and the magnitude of bend, which are necessary in order to express the bend state of the flexible portion 819, are referred to as "bend information".

The computation apparatus 10 includes a sensor 500, which is composed of a sensor driver 300 and a sensor assembly 400, and a controller 100. The details of these components will be described later.

The display 180, which is a general display device, is a liquid crystal display, a CRT display, or an organic EL display, for instance. The display 180, which is connected to the endoscope controller 820, displays an image processed by the endoscope controller 820. In addition, the display 180, which is connected to the controller 100, displays bend information or the like acquired by the computation apparatus 10.

The input device 190, which is a general device for input, is a keyboard, a pointing device such as a mouse, a tag reader, a button switch, a slider, or a dial, for instance. The input device 190 is connected to the controller 100. The input device 190 is used in order for a user to input various instructions for operating the computation apparatus 10. The input device 190 may be a storage medium. In this case, the information stored in the storage medium is input to the controller 100.

Figure 3:
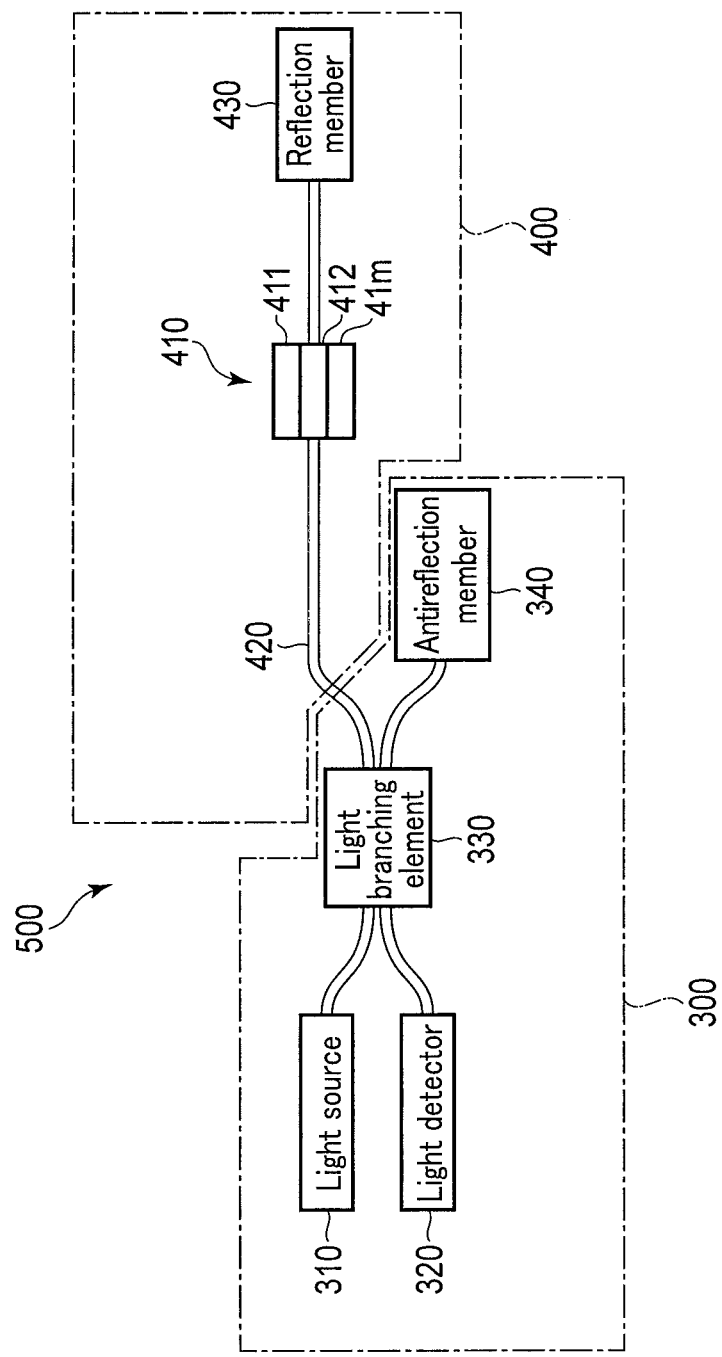
FIG. 3 is a block diagram showing an example of the configuration of a sensor.

Next, the sensor 500 of the computation apparatus 10 will be described. FIG. 3 is a block diagram showing an example of the configuration of the sensor 500, which is composed of the sensor driver 300 and the sensor assembly 400. The sensor driver 300 includes a light source 310, a light detector 320, a light branching element 330, and an antireflection member 340. The sensor assembly 400 includes a light guide 420 provided with a detection target group 410 including a plurality of detection targets; and a reflection member 430.

The light source 310 is a generally known light emission unit, such as a lamp, an LED, or a laser diode, for example. The light source 310 may further include a fluorescent element for converting wavelength.

The detection target group 410 includes at least a first detection target 411 and a second detection target 412, as shown in FIG. 3, and may further include an m-th detection target 41m. Here, "m" is an arbitrary number. The detection targets 411, 412, . . . , 41m are provided at a substantially identical position in the longitudinal direction (optical-axis direction) of the light guide 420. Hereinafter, it is assumed that the detection target group 410 is composed of the first detection target 411 and second detection target 412, and the description will be given.

Each of the detection targets 411 and 412 may be composed of, for example, a substance that reduces the intensity of light guided by the light guide 420, such as a light absorber. In another example, each of the detection targets 411 and 412 may be composed of a substance that absorbs light guided by the light guide 420 to emit light of a wavelength range that is different from the wavelength range of the guided light, such as a fluorescent material.

Figure 4:
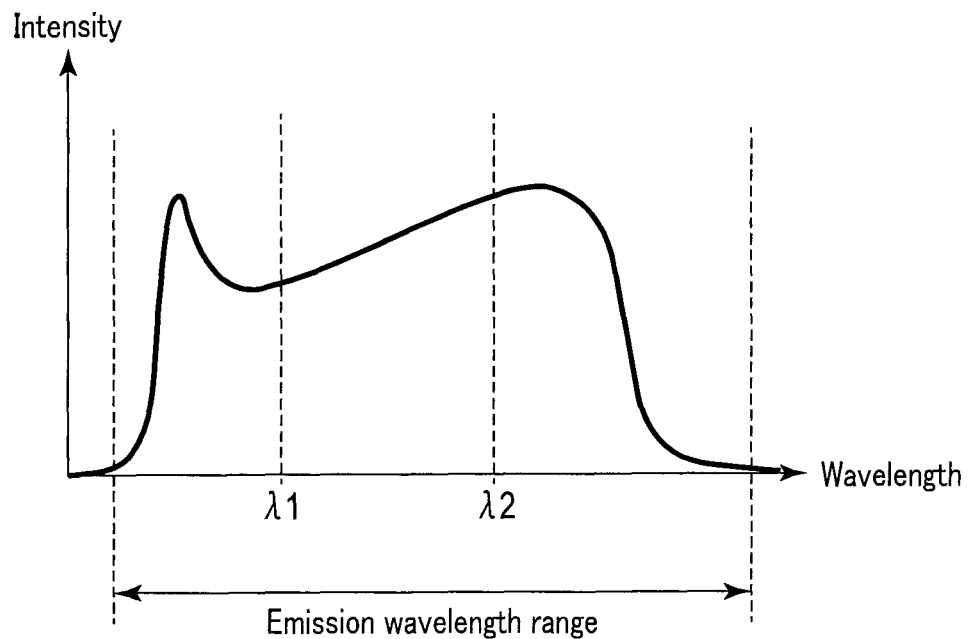
FIG. 4 is a graph showing an example of the relationship between the wavelength and the intensity of light that is emitted by a light source.

FIG. 4 is a graph showing an example of the relationship between the wavelength and the intensity of light that is emitted by the light source 310. The light source 310 emits light in an emission wavelength range including a first wavelength λ1 and a second wavelength λ2. The first wavelength λ1 is a characteristic wavelength of a spectrum that is absorbed by a light absorber of the first detection target 411 (hereinafter referred to as "first light absorber 424") constituting the detection target group 410. Here, the characteristic wavelength is, for example, a wavelength at which absorption becomes maximum (see FIG. 8). Similarly, the second wavelength λ2 is a characteristic wavelength of a spectrum that is absorbed by a light absorber of the second detection target 412 (hereinafter referred to as "second light absorber 425") constituting the detection target group 410.

The light detector 320 includes an element for spectroscopy, such as a spectroscope or a color filter, and a light receiving element such as a photodiode. The light detector 320 detects the intensity of light in a predetermined wavelength range to output detected light quantity information. Here, the detected light quantity information is information indicative of the relationship between a specific wavelength in the predetermined wavelength range and the intensity of light at the wavelength.

Figure 5:
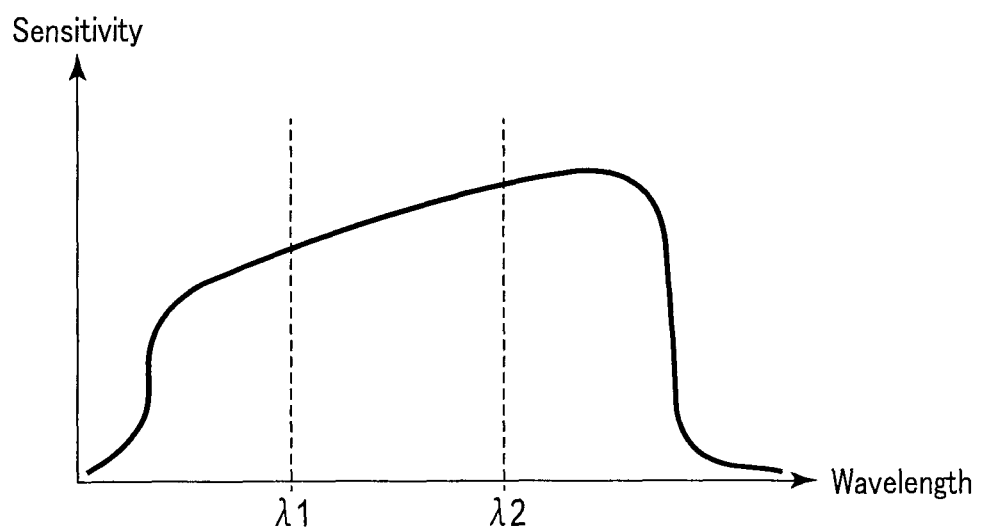
FIG. 5 is a graph showing an example of the relationship between the wavelength of light falling on a light detector and the detection sensitivity of the light detector.

FIG. 5 is a graph showing an example of the relationship between the wavelength of light falling on the light detector 320 and the detection sensitivity of the light detector 320. The light detector 320 has detection sensitivity within a wavelength range including the above-described first wavelength λ1 and second wavelength λ2. The light detector 320 outputs to the controller 100 the detected light quantity information representative of the detected light intensities, for example, at the wavelengths λ1 and λ2.

The light detector is not limited to a light detector having spectral characteristics. The light source and light detector include a mode in which the light quantity at each of a plurality of predetermined wavelength ranges is detected by a combination of light sources and light detectors. For example, the light source and light detector include a mode in which narrow-band lights are emitted from light sources in a time-sequence manner, and the light quantity at each wavelength range is detected by a wide-band light detector.

Referring back to FIG. 3, the light branching element 330 is optically connected to the light source 310 and the light detector 320. The light branching element 330 includes an optical coupler or a semitransparent mirror. The light branching element 330 guides light emitted from the light source 310 to the light guide 420, and also guides light guided by the light guide 420 to the light detector 320.

The antireflection member 340 is optically connected to the light branching element 330. The antireflection member 340 prevents part of the light emitted from the light source 310 that has not entered the light guide 420 from returning to the light detector 320.

The light guide 420, which is, for example, an optical fiber, has flexibility. The light guide 420 is connected to the light branching element 330 at its base end. As schematically shown in FIG. 1, the light guide 420 is incorporated into the insertion portion 812 along the longitudinal direction of the insertion portion 812. In the light guide 420, the detection target group 410 is arranged on a region where the bend information is to be calculated in the insertion portion 812, for example, on the flexible portion 819.

Figure 6:
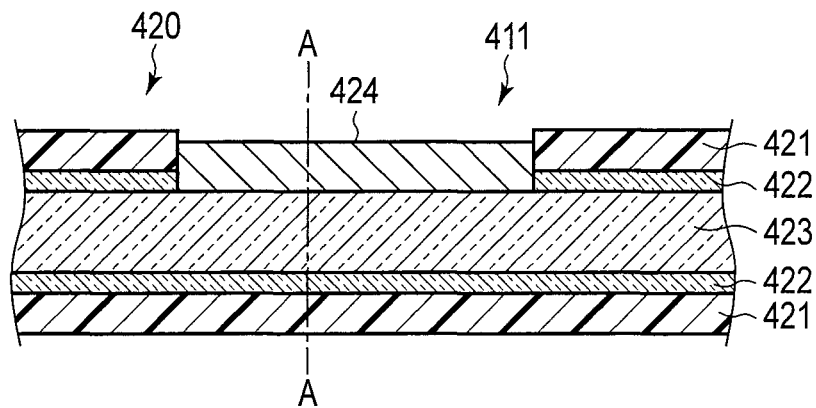
FIG. 6 is a cross-sectional view including an optical axis of a light guide.
Figure 7:
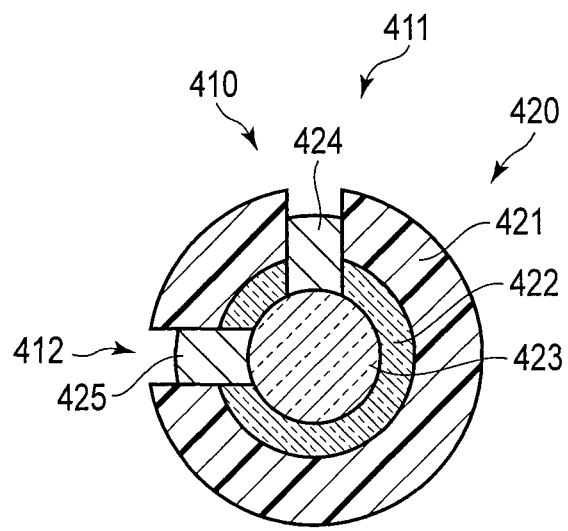
FIG. 7 is a cross-sectional view in a radial direction of the light guide taken along a line A-A in FIG. 6.

FIG. 6 is a cross-sectional view including an optical axis of the light guide 420. FIG. 7 is a cross-sectional view in a radial direction of the light guide 420 taken along a line A-A in FIG. 6. The light guide 420 includes a core 423, a clad 422 surrounding the core 423, and a jacket 421 surrounding the clad 422.

The first detection target 411 is formed by removing parts of the jacket 421 and clad 422 to expose the core 423, and then providing the first light absorber 424 on the exposed core 423. The second detection target 412 is formed by providing the second light absorber 425 in the same manner as with the first detection target 411, at substantially the same position as the first detection target 411 in the longitudinal direction of the light guide 420, and, for example, at a position substantially perpendicular to the first detection target 411 in a cross section in the radial direction of the light guide 420. Aside from the light absorber, an optical member that affects the spectrum of light guided may be used. For example, the optical member may be a wavelength conversion member (fluorescent element).

Figure 8:
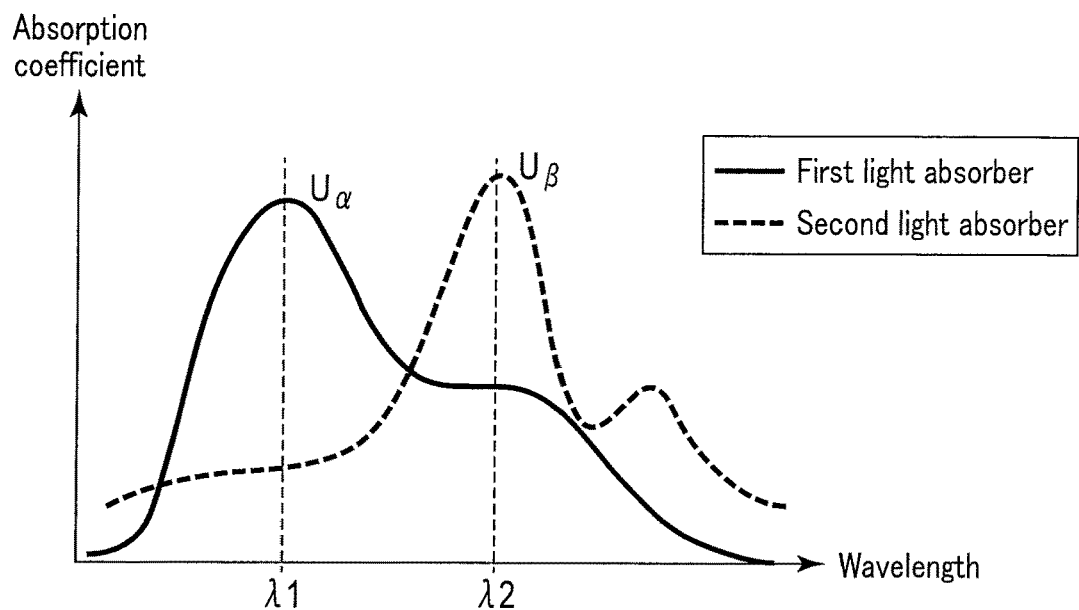
FIG. 8 is a graph showing an example of the relationship between the wavelength and the absorption coefficient of light in a first light absorber and a second light absorber.

FIG. 8 is a graph showing an example of the relationship between the wavelength and the absorption coefficient of light in the first light absorber 424 and second light absorber 425. As shown in FIG. 8, the light absorbers 424 and 425 provided in the different detection targets 411 and 412 have absorption characteristics varying depending on wavelengths, that is, have absorption characteristics being different from each other.

Figure 9A:
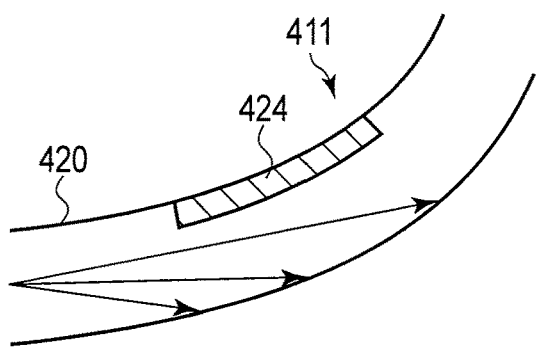
FIG. 9A is a view schematically showing transmission of light in a state in which a first detection target is bent inward.
Figure 9B:
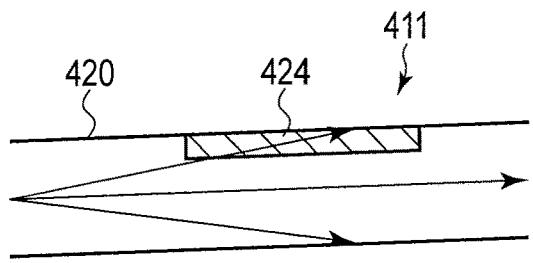
FIG. 9B is a view schematically showing transmission of light in a state in which the first detection target is straight.
Figure 9C:
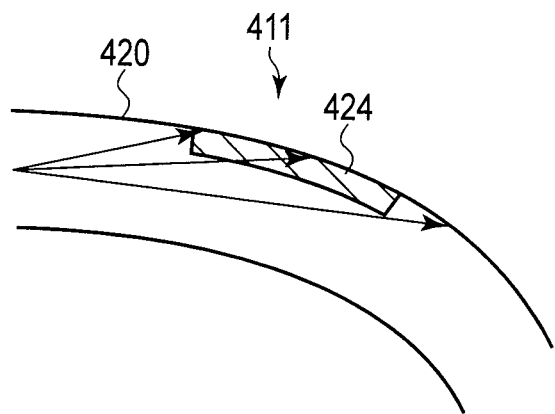
FIG. 9C is a view schematically showing transmission of light in a state in which the first detection target is bent outward.

A description will be given of the relationship between the bend state of the detection target 411, 412 and the transmission quantity of light that is guided in the light guide 420. FIGS. 9A to 9C are views schematically showing light that is guided in the vicinity of the first detection target 411 of the light guide 420. The depiction of the second detection target 412 is omitted in these Figures. As shown in FIG. 9B, when the light guide 420 is in a straight state, part of the light that is guided in the light guide 420 is absorbed in the light absorber 424. By contrast, when the light guide 420 is bent so that the light absorber 429 is located inside, since the light falling on the light absorber 424 decreases, the quantity of light absorbed by the light absorber 424 decreases (FIG. 9A). Accordingly, the transmission quantity of light guided in the light guide 420 increases. On the other hand, when the light guide 420 is bent so that the detection target group 410 is located outside, since the light falling on the light absorber 424 increases, the quantity of light absorbed by the light absorber 424 increases (FIG. 9C). Accordingly, the transmission quantity of light guided in the light guide 420 decreases.

Thus, in accordance with the bend state of the first detection target 411, the quantity of light guided in the light guide 420 varies. The same applies to the second detection target 412.

Referring back to FIG. 3, the reflection member 430 is provided at an end portion of the light guide 420, that is, a tip end thereof, on the side on which the light guide 420 is not connected to the light branching element 330. The reflection member 430 reflects the light guided from the light branching element 330 by the light guide 420 so that the light travels back toward the light branching element 330.

Next, referring back to FIG. 1, the controller 100 of the computation apparatus 10 will be described. The controller 100 can be composed of an electronic calculator such as a personal computer. The controller 100 includes an arithmetic operator 101, an endoscope bend information calculator 140, a light detector driver 150, and an output unit 160.

The arithmetic operator 101 is composed of, for example, a device including a CPU or an ASIC. The arithmetic operator 101 includes an input unit 130, a storage 120, and a bend information arithmetic operator 110.

Detected light quantity information is input to the input unit 130 from the light detector 320 of the sensor driver 300. The input unit 130 transmits the input detected light quantity information to the bend information arithmetic operator 110. In addition, bend coefficients (to be described later) of the detection target group 410 is input to the input unit 130. Further, information output from the endoscope controller 820 is input to the input unit 130. The input unit 130 transmits these input information pieces to the bend information arithmetic operator 110 or the light detector driver 150.

The storage 120 stores various kinds of information necessary for arithmetic operations that are executed by the bend information arithmetic operator 110. The storage 120 stores, for example, programs including a calculation algorithm, the bend coefficients of the detection target group 410, alight quantity information relationship, reference light quantity information, and intensity modulation information.

The bend information arithmetic operator 110 calculates the bend information of the detection target group 410, based on the detected light quantity information acquired through the input unit 130, and the light quantity information relationship, reference light quantity information, intensity modulation information, and bend coefficients, which are stored in the storage 120 and will be described later. The bend information arithmetic operator 110 includes a first arithmetic operator 212 and a second arithmetic operator 214. The first arithmetic operator 212 calculates light quantity variation information of each of the detection targets 411 and 412, based on the detected light quantity information, which is acquired through the input unit 130, and the light quantity information relationship, reference light quantity information, and intensity modulation information, which are stored in the storage 120. The second arithmetic operator 214 calculates bend information in the detection target group 410, based on the light quantity variation information, which is calculated by the first arithmetic operator 212, and the bend coefficients, which are stored in the storage 120. The bend information arithmetic operator 110 transmits the calculated bend information to the endoscope bend information calculator 140 and output unit 160. In addition, the bend information arithmetic operator 110 outputs to the light detector driver 150 the information that relates to the operation of the light detector 320 and is necessary for the bend information calculation, such as a gain of the light detector 320.

The endoscope bend information calculator 140 includes, for example, a CPU or an ASIC. Based on the bend information of the detection target group 410 calculated by the bend information arithmetic operator 110, the endoscope bend information calculator 140 calculates the bend information of the insertion portion 812 in which the detection target group 410 is arranged. The calculated bend information is transmitted to the output unit 160. The endoscope bend information calculator 140 may be assembled in the bend information arithmetic operator 110.

The light detector driver 150 generates a driving signal of the light detector 320, based on the information acquired from the input unit 130 or the bend information arithmetic operator 110. By the driving signal, the light detector driver 150 switches on/off the operation of the light detector 320, for example, based on the user's instruction that is acquired through the input unit 130, or adjusts the gain of the light detector 320, based on the information acquired from the bend information arithmetic operator 110. The light detector driver 150 may be configured to also control the operation of the light source 310. The light detector driver 150 transmits the generated driving signal to the output unit 160.

The output unit 160 outputs to the display 180 the bend information of the detection target group 410 acquired from the bend information arithmetic operator 110 or the bend information of the insertion portion 812 acquired from the endoscope bend information calculator 140. The output unit 160 also outputs these acquired pieces of bend information to the endoscope controller 820. The output unit 160 also outputs the driving signal from the light detector driver 150 to the light detector 320.

The operation of the endoscope system 1 and computation apparatus 10 of the present embodiment will be described.

The insertion portion 812 of the endoscope 810 is inserted into an insertion target by the user. During insertion, the insertion portion 812 bends in accordance with the shape of the insertion target. The endoscope 810 acquires an image signal by the observation optical system and the image sensor in the insertion portion 812. The acquired image signal is transmitted to the image processor 822 of the endoscope controller 820. The image processor 822 creates an image of the inside of the insertion target, based on the acquired image signal. The image processor 822 causes the display 180 to display the created image.

When the user wishes to cause the display 180 to display the bend information of the insertion portion 812, or when the user wishes to cause the endoscope controller 820 to perform various operations using the bend information of the insertion portion 812, the user inputs the corresponding instruction to the controller 100 through the input device 190. Then, the computation apparatus 10 operates.

When the computation apparatus 10 operates, the light source 310 of the sensor driver 300 emits light of a predetermined emission wavelength range. The light emitted from the light source 310 is guided to the light guide 420 of the sensor assembly 400 through the light branching element 330. The guided light transmits in the light guide 420 from the tip end side to the base end side. At this time, the light quantity in the light guide 420 varies in accordance with the bend state of the detection target group 410 provided on the light guide 420, and the quantity of transmitted light varies at each wavelength. Then, the light is reflected and returned by the reflection member 430, and transmits in the light guide 420 from the base end side to the tip end side. The reflected light reaches the light detector 320 through the light branching element 330. The light detector 320 detects the intensity of the reached light at each wavelength.

The light detector 320 outputs detected light quantity information, which relates to the wavelength and the detected light intensity, to the input unit 130 of the controller 100. The input detected light quantity information is acquired by the bend information arithmetic operator 110 from the input unit 130, and the bend information arithmetic operator 110 calculates the bend information of the detection target group 410.

The calculated bend information of the detection target group 410 is acquired by the endoscope bend information calculator 140. Based on the acquired bend information, the endoscope bend information calculator 140 calculates the bend information of the insertion portion 812.

The bend information of the detection target group 410 calculated by the bend information arithmetic operator 110, or the bend information of the insertion portion 812 calculated by the endoscope bend information calculator 140, is acquired by the endoscope controller 820 through the output unit 160. Based on these acquired pieces of bend information, the endoscope controller 820 controls the operation of the endoscope 810. In addition, these pieces of bend information are displayed on the display 180 through the output unit 160.

Furthermore, the information input to the input unit 130 and the bend information of the detection target group 410 calculated by the bend information arithmetic operator 110 are acquired by the light detector driver 150. Based on the acquired information, the light detector driver 150 transmits a driving signal to the light detector 320 through the output unit 160 to control the operation of the light detector 320.

In this manner, according to the computation apparatus 10, the bend information of the detection target group 410 is acquired by the arithmetic operator 101. In addition, based on the acquired bend information, the endoscope bend information calculator 140 calculates the bend information of the insertion portion 812. This allows the user to understand the bend information of the detection target group 410 or the insertion portion 812 while operating the endoscope 810. In addition, the endoscope controller 820 is allowed to properly control the operation of the endoscope 810 in accordance with these pieces of bend information.

A description will be given of arithmetic operations that are executed by the arithmetic operator 101 in the computation apparatus 10 of the present embodiment.

To begin with, the information to be prepared in advance before using the computation apparatus 10 will be described. Detected light quantity information $D_{\lambda,n}$ of light of wavelength $\lambda n$, which is detected by the light detector 320, is given by the following equation (1).

$$D_{\lambda,n}=E_{\lambda,n} \times A_{\lambda,2} \times B_{\lambda,n} \times C_{\lambda,n} \quad (1)$$

Here $E_{\lambda,n}$ is an emission light quantity about light of wavelength $\lambda n$, which is emitted from the light source 310; $A_{\lambda,n}$ is an absorptivity of light of wavelength $\lambda n$ in the first light absorber 424; $E_{\lambda,n}$ is an absorptivity of light of wavelength $\lambda n$ in the second light absorber 425; and $C_{\lambda,n}$ is an absorptivity of light of wavelength $\lambda n$ by members other than the detection target group 410, such as the light branching element 330, light guide 420, and reflection member 430, which are included in an optical path along which light transmits in the sensor driver 300 and sensor assembly 400.

The emission light quantity $E_{\lambda,n}$ and absorptivity $C_{\lambda,n}$ do not depend on the direction of bend or the magnitude of bend of the detection target group 410. Accordingly, equation (1) representing the detected light quantity information $D_{\lambda,n}$ is rewritten as equation (2).

$$D_{\lambda,n} = I_{\lambda,n} \times F_{\lambda,n} \times G_{\lambda,n} \quad (2)$$

Here $I_{\lambda,n}$ is reference light quantity information, and is a light quantity about light of wavelength λn, which is detected by the light detector 320 when the detection target group 410 (each detection target 411, 412) is in a reference predetermined shape (hereinafter referred to as "reference bend state"). In addition, $F_{\lambda,n}$ is a variation ratio in light quantity occurring due to light absorption by only the first detection target 411, and is a ratio between a light quantity about light of wavelength λn and the reference light quantity information $I_{\lambda,n}$ during the second detection target 412 is in the reference bend state. $G_{\lambda,n}$ is a variation ratio in light quantity occurring due to light absorption by only the second detection target 412, and is a ratio between a light quantity about light of wavelength λn and the reference light quantity information $I_{\lambda,n}$ during the first detection target 411 is in the reference bend state.

The absorption coefficient of light in each light absorber 424, 425 of each detection target 411, 412 of the detection target group 410 varies in accordance with the direction of bend of the detection target group 410, for example, the above-described angle θ, and the magnitude of bend, for example, the curvature κ. Accordingly, the variation ratios $F_{\lambda,n}$ and $G_{\lambda,n}$ in the first detection target 411 and second detection target 412 of the detection target group 410 are given by the following equations (3) and (4), respectively.

$$F_{\lambda n} = e^{\alpha(\theta,\kappa) \cdot U_{\alpha \lambda n}} \quad (3)$$

$$G_{\lambda n} = e^{\beta(\theta,\kappa) \cdot U_{\beta \lambda n}} \quad (4)$$

Here functions $\alpha(\theta, \kappa)$ and $\beta(\theta, \kappa)$ are, respectively, bend coefficients of the first detection target 411 and second detection target 412 of the detection target group 410. $U_{\alpha\lambda n}$ and $U_{\beta\lambda n}$ are, respectively, pieces of intensity modulation information of the first detection target 411 and second detection target 412 of the detection target group 410. From equations (2), (3), and (4), the following equation (5) is obtained.

$$D_{\lambda n}(\theta, \kappa) = I_{\lambda n} \cdot e^{\alpha(\theta,\kappa) \cdot U_{\alpha \lambda n}} \cdot e^{\beta(\theta,\kappa) \cdot U_{\beta \lambda n}} \quad (5)$$

In equation (5), the left side expresses detected light quantity information in an arbitrary bend state, and the right side expresses a calculated light quantity value that is generated based on the reference light quantity information, bend coefficients, and intensity modulation information. By taking a natural logarithm of both sides of equation (5), alight quantity information relationship expressed by the following equation (6) is obtained.

$$\ln[D_{\lambda n}(\theta,\kappa)] = \ln(I_{\lambda n}) + \alpha(\theta,\kappa) \cdot U_{\alpha\lambda n} + \beta(\theta,\kappa) \cdot U_{\beta\lambda n} \quad (6)$$

By taking the logarithm, the right side of equation (5) is expressed by addition. Thereby, equation (6) becomes easier to calculate, than equation (5).

As the reference bend state for determining the reference light quantity information $I_{\lambda,n}$, for example, the case in which the detection target group 410 is in the straight shape is adopted, that is, the case is adopted in which the curvature of the detection target 411, 412 is 0, and the radius of curvature is ∞. However, the reference bend state is not limited to this, and the detection target group 410 may be in a shape other than the straight shape. Hereinafter, the case in which the detection target group 410 is in the straight shape is adopted as the reference bend state. For the purpose of convenience, it is assumed that the angle θ of the detection target group 410 in the straight shape is 0.

Figure 10:
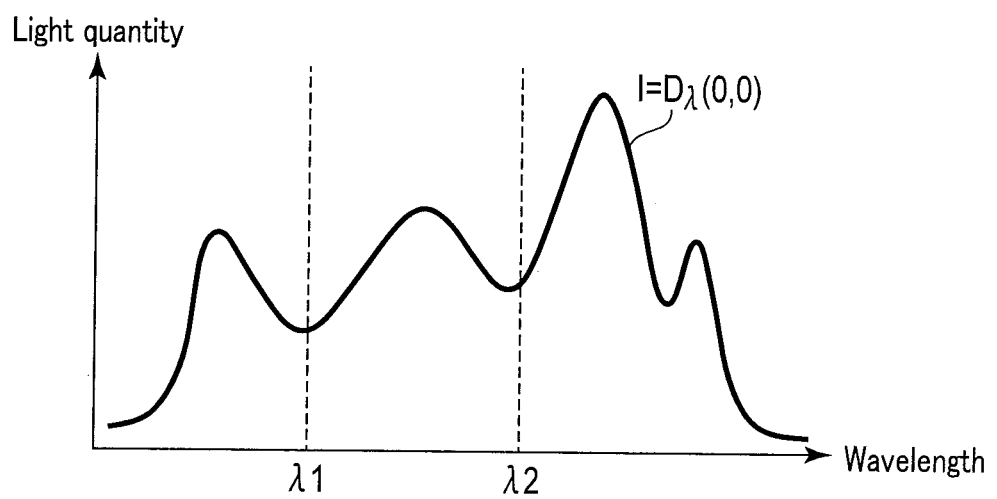
FIG. 10 is a graph showing an example of the relationship between the wavelength and the reference light quantity information.

FIG. 10 is a graph showing an example of the relationship between the wavelength and the reference light quantity information. The reference light quantity information $I_{\lambda,n}$ is given by a light quantity $D_{\lambda,n}(0, 0)$ during the detection target group 410 is in the reference bend state, that is, during θ=0, and κ=0. Specifically, the reference light quantity information $I_{\lambda,n}$ is given by the following equation (7).

$$I_{\lambda n} = D_{\lambda n}(0,0) \quad (7)$$

The bend coefficients $\alpha(\theta, \kappa)$ and $(\theta, \kappa)$ are obtained by varying the above-described angle θ and curvature κ of the detection target group 410 within possible ranges. The wavelengths λn, which are used for arithmetic operations, are wavelengths λ1 and λ2 of light respectively absorbed in the detection targets 411 and 412. FIG. 11 is a graph showing an example of the bend coefficient $\alpha(\theta, \kappa)$ obtained with respect to the first wavelength λ1, that is, the bend coefficient $\alpha(\theta, \kappa)$ of the first detection target 411. FIG. 12 is a graph showing an example of the bend coefficient $\beta(\theta, \kappa)$ obtained with respect to the second wavelength λ2, that is, the bend coefficient $\beta(\theta, \kappa)$ of the second detection target 412. In this manner, since the amplitude and phase differ depending on curvature, the angle θ and curvature κ are computable. FIG. 11 and FIG. 12 show, respectively, the bend coefficients with respect to two curvatures $\kappa_a$ and $\kappa_b$ ($\kappa_a > \kappa_b$). However, the obtained bend coefficients are not limited to these, and the relationship between the angle θ and the bend coefficient in the detection target group 410 is obtained with respect to various curvatures κ.

Each of the bend coefficients $\alpha(\theta, \kappa)$ and $\beta(\theta, \kappa)$ can be expressed by a periodic function. For example, the bend coefficients $\alpha(\theta, \kappa)$ and $\beta(\theta, \kappa)$ can be expressed approximately by sine functions of the following equations (8) and (9), respectively.

$$\alpha(\theta,\kappa) = a_\alpha(\kappa) \cdot \sin[\theta + b_\alpha(\kappa)] + c_\alpha(\kappa) \quad (8)$$

$$\beta(\theta,\kappa) = a_\beta(\kappa) \cdot \sin[\theta + b_\beta(\kappa)] + c_\beta(\kappa) \quad (9)$$

Here $a_\alpha(\kappa)$ and $a_\beta(\kappa)$ are amplitudes, $b_\alpha(\kappa)$ and $b_\beta(\kappa)$ are phases, and $c_\alpha(\kappa)$ and $c_\beta(\kappa)$ are offsets.

Incidentally, the periodic function is not limited to the periodic function expressed by a first-degree sine wave, and, for example, the precision is enhanced if use is made of a Fourier series in which higher-degree sine waves as functions $\alpha(\theta, \kappa)$ and $\beta(\theta, \kappa)$ are combined.

The bend coefficients and reference light quantity information are acquired in advance, for example, when the endoscope system 1 is manufactured, or when the endoscope system 1 is assembled, and are prestored in the storage 120. Alternatively, the bend coefficients and reference light quantity information may be acquired at each time of use.

Figure 13:
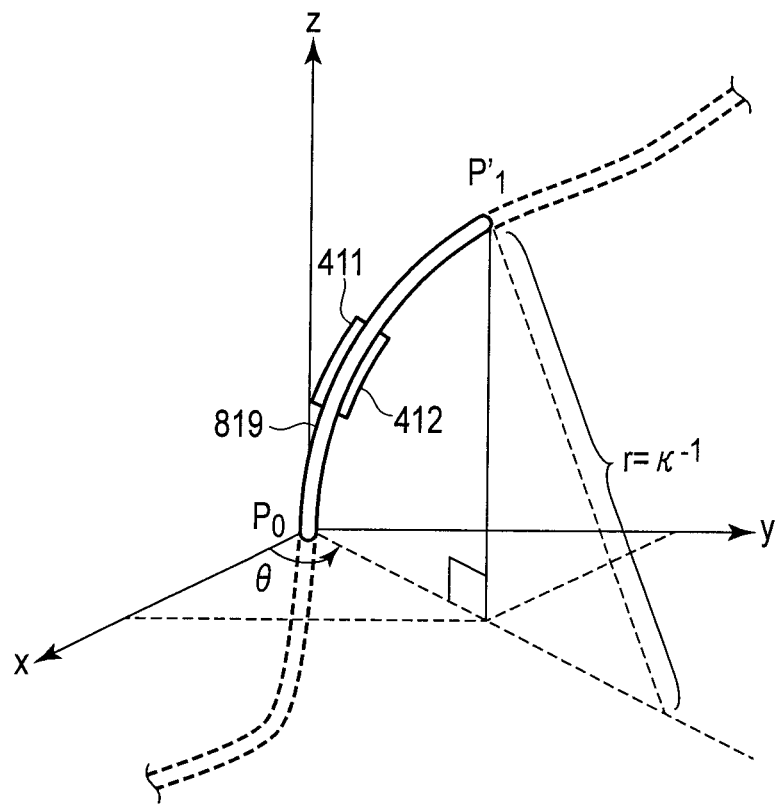
FIG. 13 is a view showing a state in which a flexible portion with a length L including a detection target group is bent at an angle θ and a curvature κ.
Figure 14:
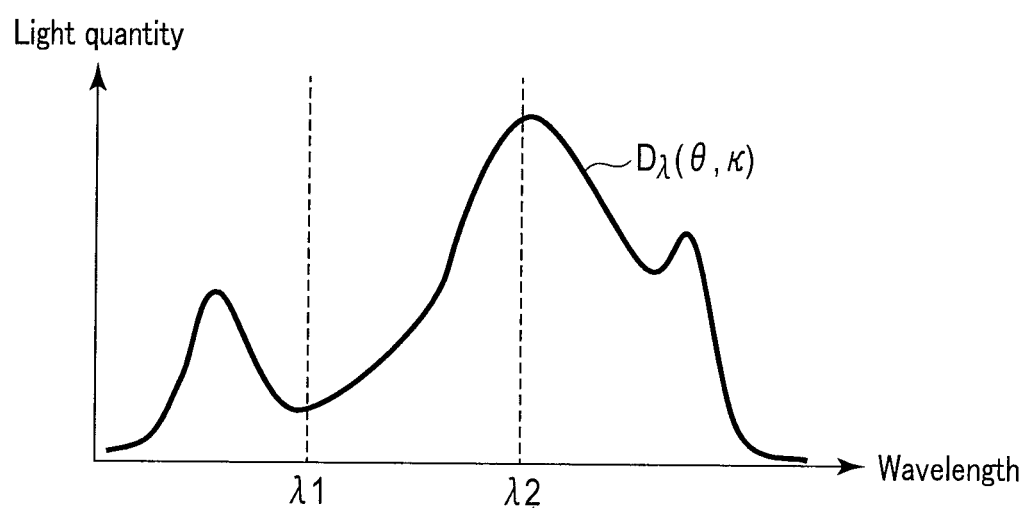
FIG. 14 is a graph showing an example of a detection light quantity in the bend state of FIG. 13.

Next, arithmetic operations to be executed by the arithmetic operator 101 at the time of using the computation apparatus 10 will be described. The state is now considered in which the flexible portion 819 with a length L including the detection target group 140 is bent at an angle θ and a curvature κ shown in FIG. 13. FIG. 14 is a graph showing an example of the relationship between the wavelength and the detected light quantity in the bend state.

In the present embodiment, the angle θ and curvature κ in the detection target group 410 are calculated as follows.

To begin with, in the first arithmetic operator 212, based on the detected light quantity information $D_{\lambda 1}$ and $D_{\lambda 2}$ at the first wavelength λ1 and second wavelength λ2 detected by the light detector 320, first-degree simultaneous equations with two variables expressed by the following equations (10) obtained according to the light quantity information relationship are solved with respect to α(θ, κ) and β(θ, κ).

$$\begin{cases} \ln[D_{\lambda 1}(\theta, \kappa)] - \ln(I_{\lambda 1}) = \alpha(\theta, \kappa) \cdot U_{\alpha_{\lambda 1}} + \beta(\theta, \kappa) \cdot U_{\beta_{\lambda 1}} \\ \ln[D_{\lambda 2}(\theta, \kappa)] - \ln(I_{\lambda 2}) = \alpha(\theta, \kappa) \cdot U_{\alpha_{\lambda 2}} + \beta(\theta, \kappa) \cdot U_{\beta_{\lambda 2}} \end{cases} \quad (10)$$

The reference light quantity information $I_{\lambda 1}$, $I_{\lambda 2}$ and intensity modulation information $U_{\alpha\lambda 1}$, $U_{\beta\lambda 1}$, $U_{\alpha\lambda 2}$, $U_{\beta\lambda 2}$ are obtained in advance and stored in the storage 120, as described above. Accordingly, in the first arithmetic operator 212, the light quantity variation information α and β in the first detection target 411 and second detection target 412 of the detection target group 410 can be calculated based on the detected light quantity information $D_{\lambda 1}$, $D_{\lambda 2}$, reference light quantity information $I_{\lambda 1}$, $I_{\lambda 2}$, and intensity modulation information $U_{\alpha\lambda 1}$, $U_{\beta\lambda 1}$, $U_{\alpha\lambda 2}$, $U_{\beta\lambda 2}$.

Next, in the second arithmetic operator 214, simultaneous equations with two variables expressed by the following equations (11) obtained according to the light quantity variation information α and β calculated by the first arithmetic operator 212 and the bend coefficients α(θ, κ) and β(θ, κ) stored in the storage 120 are solved with respect to θ and κ.

$$\begin{cases} \alpha(\theta, \kappa) = a_\alpha(\kappa) \cdot \sin[\theta + b_\alpha(\kappa)] + c_\alpha(\kappa) \\ \beta(\theta, \kappa) = a_\beta(\kappa) \cdot \sin[\theta + b_\beta(\kappa)] + c_\beta(\kappa) \end{cases} \quad (11)$$

In this manner, the bend information of the detection target group 410, that is, the angle θ and curvature κ in the detection target group 410, in other words, the direction of bend and the magnitude of bend of the detection target group 410, can be calculated. In the meantime, the light quantity information relationship is not limited to the relationship expressed by the above-described function form, and may be a light quantity information relationship expressed by a table (lookup table) in which the relationship between the wavelength and the light quantity is stored.

Although the curvature is set as the parameter representing the magnitude of bend of the detection target group, and the bend information computation arithmetic operation using the bend coefficients has been described, it is possible to adopt, as the parameter representing the magnitude of bend, some other parameter, such as a radius of curvature, and a bend information computation arithmetic operation using the bend coefficients corresponding to that parameter.

Figure 15:
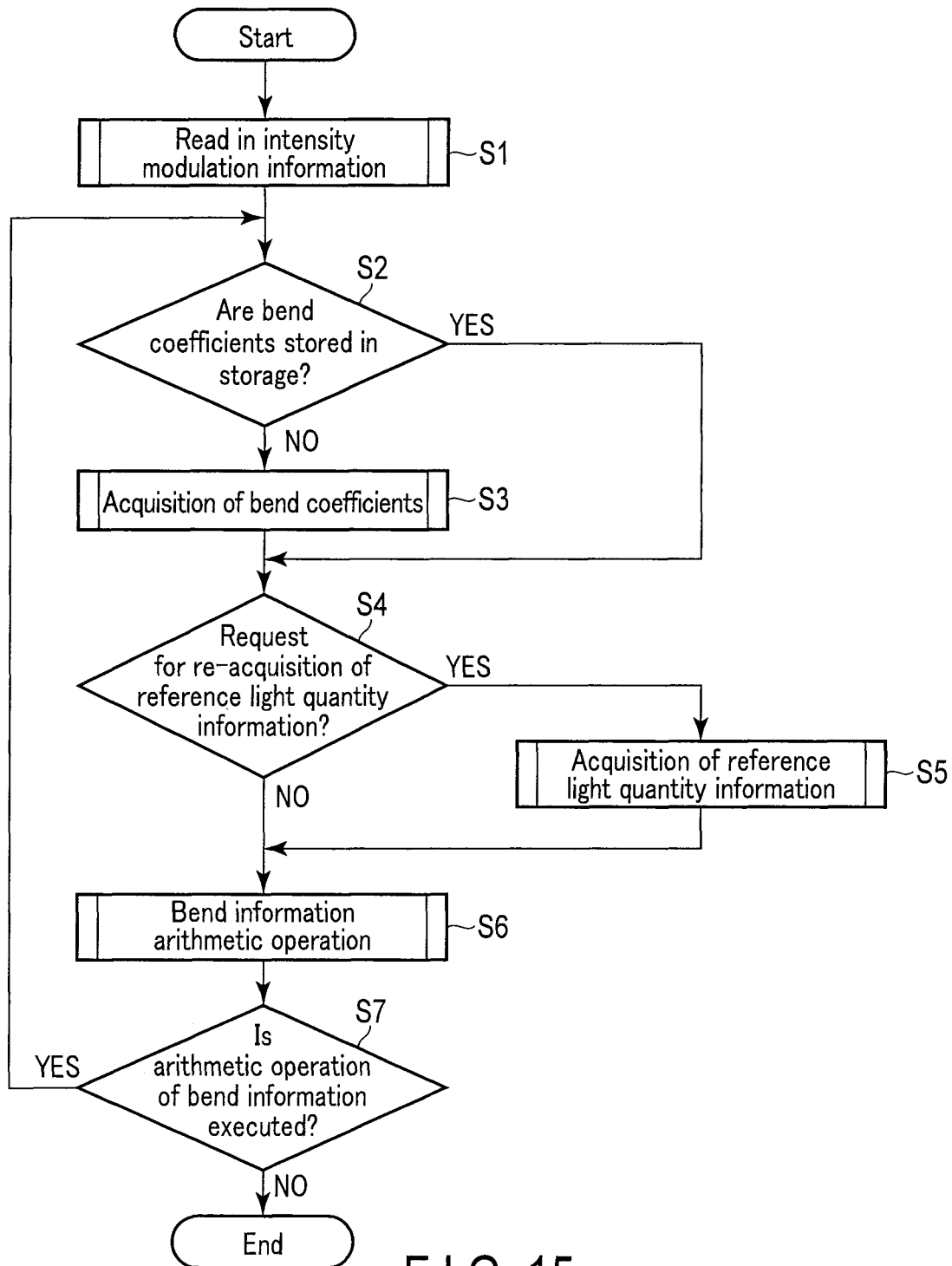
FIG. 15 is a flowchart showing the flow of a process in a controller.

FIG. 15 is a flowchart showing the flow of a process in the controller 100. In step S1, the controller 100 reads in the intensity modulation information, which is stored in the storage 120.

Storing of the intensity modulation information in the storage 120 is performed, for example, at a time of factory shipment. Alternatively, the intensity modulation information, which is stored in a portable storage medium, may be read in from the input device 190.

The intensity modulation information is acquired, for example, in the following manner. A light absorber, whose intensity modulation information is to be acquired, is disposed in a detection target of a sensor including a light guide on which only a single detection target is formed. Reference light quantity information is obtained with the light guide being in the reference bend state. Detected light quantity information is obtained with the detection target bent in an arbitrary shape. The detected light quantity information in the arbitrary shape is divided by the reference light quantity information, and then a natural logarithm of the result of the division is taken.

In step S2, the controller 100 determines whether the bend coefficients are stored in the storage 120 or not. If it is determined that the bend coefficients are not stored (NO), the process advances to step S3, and the controller 100 acquires the bend coefficients.

FIG. 16 is a flowchart showing an example of acquisition of the bend coefficients. In step S31, the controller 100 acquires reference light quantity information $I_\lambda$.

FIG. 17 is a flowchart showing an example of acquisition of the reference light quantity information. In step S311, the controller 100 sets the detection target group 410 in the reference bend state (the straight shape in the present embodiment). In the case in which the detection target group 410 is manually set in the reference bend state, the controller 100 confirms in step S311 whether the detection target group 410 is set in the reference bend state. In step S312, the controller 100 acquires reference light quantity information $I_\lambda$ in the reference bend state (equation (7)). In step S313, the acquired reference light quantity information $I_\lambda$ is stored in the storage 120. Then, the acquisition of the reference light quantity information $I_\lambda$ is completed, and the process advances to step S32.

Referring back to FIG. 16, in step S32, the controller 100 acquires detected light quantity information by bending that part of the light guide 420 where the detection target group 410 is disposed, in the direction of bend and with curvature that are already known. The detected light quantity information can be acquired, for example, by manually varying the direction of bend, or by mechanical varying it with a bend setting mechanism (not shown), with the magnitude of bend being adjusted to the curvature $\kappa_a$, $\kappa_b$. Alternatively, a calibration device may be used at the time of bending with the known direction of bend and curvature.

In step S33, using the light quantity information relationship, decomposition is made into light quantity variation information components of the respective detection targets, and the bend coefficients α(θ, κ) and β(θ, κ) of the respective detection targets are calculated. Since the bend state (direction of bend and curvature) is known, the graphs shown in FIG. 11 and FIG. 12 can be plotted, and an approximate expression of the bend coefficient of each detection target can be obtained.

In step S34, the acquired bend coefficient of each detection target is stored in the storage 120. Thus, the acquisition of the bend coefficients is completed.

Referring back to FIG. 15, after the acquisition of the bend coefficients in step S3, or alternatively if it is determined in step S2 that the bend coefficients are stored in the storage 120 (YES), the process goes to step S4. The case in which "YES" is determined in step S2 is, for example, a case in which the acquisition of the bend coefficients has been made at a time of the factory shipment of the endoscope system 1 or at a time of assembly of the endoscope system 1.

In step S4, the controller 100 determines whether to receive a request for re-acquisition of the reference light quantity information. If it is determined that it receives the request (YES), the process advances to step S5. Then, in step S5, the controller 100 acquires the reference light quantity information by the above-described subroutine (steps S311 to S313) of the acquisition of reference light quantity information. The case in which such a request for re-acquisition is made is, for example, a case in which a connection to a controller, which is different from the above-described controller 100, has been made, or a case in which the sensor driver 300 and the sensor assembly 400 has been disconnected and reconnected.

After the acquisition of the reference light quantity information $I_\lambda$ in step S5, or if it is determined in step S4 that it does not receive the request (NO), the process advances to step S6, and the arithmetic operator 101 of the controller 100 executes bend information arithmetic operations of the detection target group 410.

Figure 18:
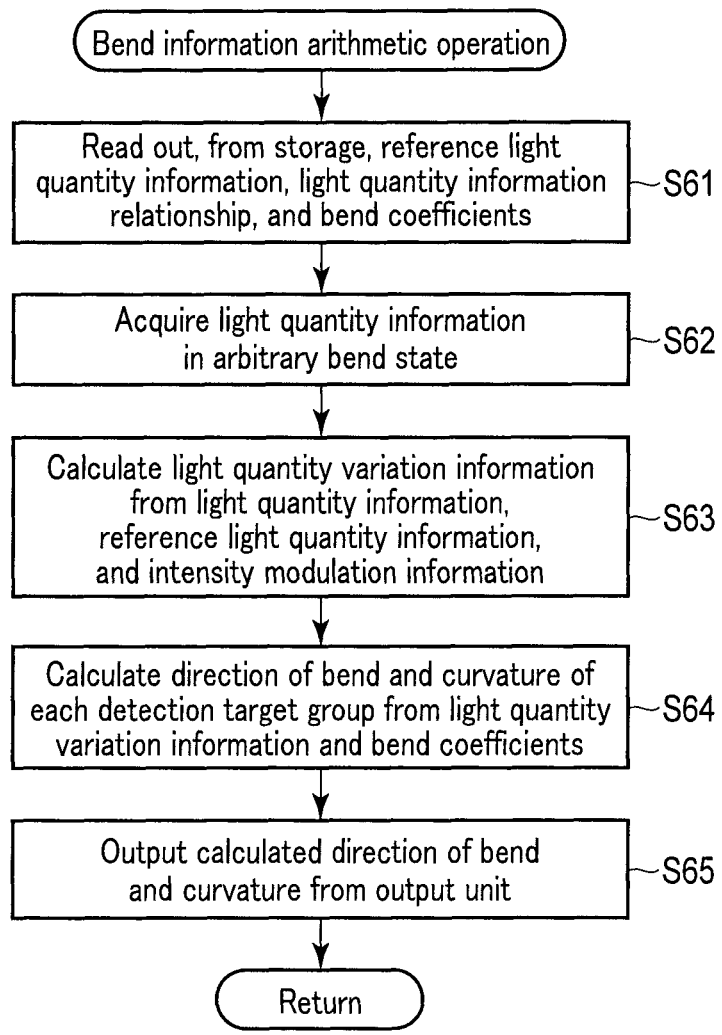
FIG. 18 is a flowchart showing an example of a bend information arithmetic operation processing.

FIG. 18 is a flowchart showing an example of a bend information arithmetic operation processing. In step S61, the bend information arithmetic operator 110 reads out, from the storage 120, the light quantity information relationship, reference light quantity information $I_\lambda$, intensity modulation information $U_{\alpha\lambda 1}$, $U_{\beta\lambda 1}$, $U_{\alpha\lambda 2}$, $U_{\beta\lambda 2}$, and bend coefficients $\alpha(\theta, \kappa)$ and $\beta(\theta, \kappa)$. In step S62, the bend information arithmetic operator 110 acquires detected light quantity information $D_{\lambda 1}$, $D_{\lambda 2}$ of light of wavelength $\lambda 1$, $\lambda 2$ in an arbitrary bend state, by the light detector 320 through the input unit 130.

In step S63, the first arithmetic operator 212 acquires the light quantity variation information $\alpha$, $\beta$, from the detected light quantity information $D_{\lambda 1}$, $D_{\lambda 2}$, light quantity information relationship, reference light quantity information $I_\lambda$, and intensity modulation information $U_{\alpha\lambda 1}$, $U_{\beta\lambda 1}$, $U_{\alpha\lambda 2}$, $U_{\beta\lambda 2}$. Specifically, with $D_{\lambda 1}(\theta, \kappa)=D_{\lambda 1}$, and $D_{\lambda 2}(\theta, \kappa)=D_{\lambda 2}$, the first-degree simultaneous equations with two variables expressed by equations (10) are solved, so that the values of $\alpha(\theta, \kappa)$ and $\beta(\theta, \kappa)$ are calculated. The thus calculated values of $\alpha(\theta, \kappa)$ and $\beta(\theta, \kappa)$ are, respectively, the light quantity variation information $\alpha$ and $\beta$ in the detection targets 411 and 412. Since these first-degree simultaneous equations with two variables can be solved by a matrix arithmetic operation, the load of calculation is light.

In step S64, the second arithmetic operator 214 calculates the angle $\theta$ and curvature $\kappa$ in the detection target group 410, that is, the direction of bend and the magnitude of bend of the detection target group 410, from the light quantity variation information $\alpha$, $\beta$ calculated by the first arithmetic operator 212, and the approximate expression of the bend coefficients $\alpha(\theta, \kappa)$, $\beta(\theta, \kappa)$ expressed in equation (8) and equation (9). Specifically, with $\alpha(\theta, \kappa)=\alpha$, and $\beta(\theta, \kappa)=\beta$, the simultaneous equations with two variables expressed by equations (11) are solved, so that the values of $\theta$ and $\kappa$ are calculated.

In step S65, the bend information arithmetic operator 110 transmits the calculated angle $\theta$ and curvature $\kappa$ to the output unit 160. Thus, the bend information arithmetic operation is completed.

Referring back to FIG. 15, after the bend information arithmetic operation processing in step S6, the process advances to step S7. In step S7, the controller 100 determines whether or not to execute the arithmetic operation of bend information. If it is determined that the arithmetic operation of bend information is executed (YES), the process returns to step S2, and the processes of step S2 onwards are repeated. If it is determined that the arithmetic operation of bend information is not executed (NO), the process terminates.

The bend coefficients depend on only the absorption characteristics of the light absorbers 424 and 425 of the detection target group 410, and do not depend on the characteristics of the light source 310 and light detector 320. Accordingly, it is possible to separate the respective structural components of the sensor driver 300, and to use, for example, a light source to emit light of a predetermined emission wavelength range, and a light detector having detection sensitivity over all wavelengths that the controller 100 requires. In other words, the bend coefficient can be acquired by some other light source and light detector, and replacement with some other sensor driver is possible.

According to the present embodiment, the light guide 420 constituting the sensor assembly 400 is provided with the detection target group 410 including the plural detection targets formed at a substantially identical position in the longitudinal direction of the light guide 420. In order to compute the bend information of the detection target group 410, wavelengths the number of which is equal to or greater than the number of detection targets are used. The detected light quantity information of each of these wavelengths in the detection target group 410 is detected by the light detector 320 of the sensor driver 300. Then, the bend information arithmetic operator 110 first calculates, in the first arithmetic operator 212, the light quantity variation information, based on the detected light quantity information, and the light quantity information relationship prestored in the storage 120, and then computes, in the second arithmetic operator 214, the bend information of the detection target group 410, accordingly the insertion portion 812, based on the calculated light quantity variation information, and the bend coefficient prestored in the storage 120. In this manner, according to the present embodiment, a bend information computation apparatus capable of computing the bend information can be provided.

Additionally, according to the present embodiment, the bend coefficient of light in the detection target group 410 is used in order to calculate the bend information. Therefore, the bend information arithmetic operation can be executed without depending on the spectrum of the light source 310 of the sensor driver 300 and the spectral sensitivity of the light detector 320.

Additionally, according to the present embodiment, no information of the distance between the light source 310 and the detection target group 410 provided on the light guide 420 is needed for the bend information arithmetic operation. Therefore, the bend information arithmetic operation can be executed without taking into account the positional relationship between the light source 310 and the detection target group 410.

Additionally, according to the present embodiment, the absorption and the loss of light by the light branching element 330 of the sensor driver 300 or by the reflection member 430 of the sensor assembly 400 are constant without depending on the magnitude of bend of the detection target group 410. Accordingly, the reference light quantity information is calculated in the state in which the loss is included. Therefore, the calculation can be made without giving additional consideration to the influence of the light branching element 330 and the reflection member 430.

The first embodiment may also be implemented in the following modes.

(First Mode)

The request for re-acquisition of the reference light quantity information, which is determined in step S4, occurs, for example, in a case in which the light branching element 330 of the sensor driver 300 and the light guide 420 of the sensor assembly 400 have been disconnected and reconnected. The controller 100 may be configured to determine, in such a case, whether the connection is maintained, that is, whether the disconnection and reconnection have been made.

(Second Mode)

Figure 19:
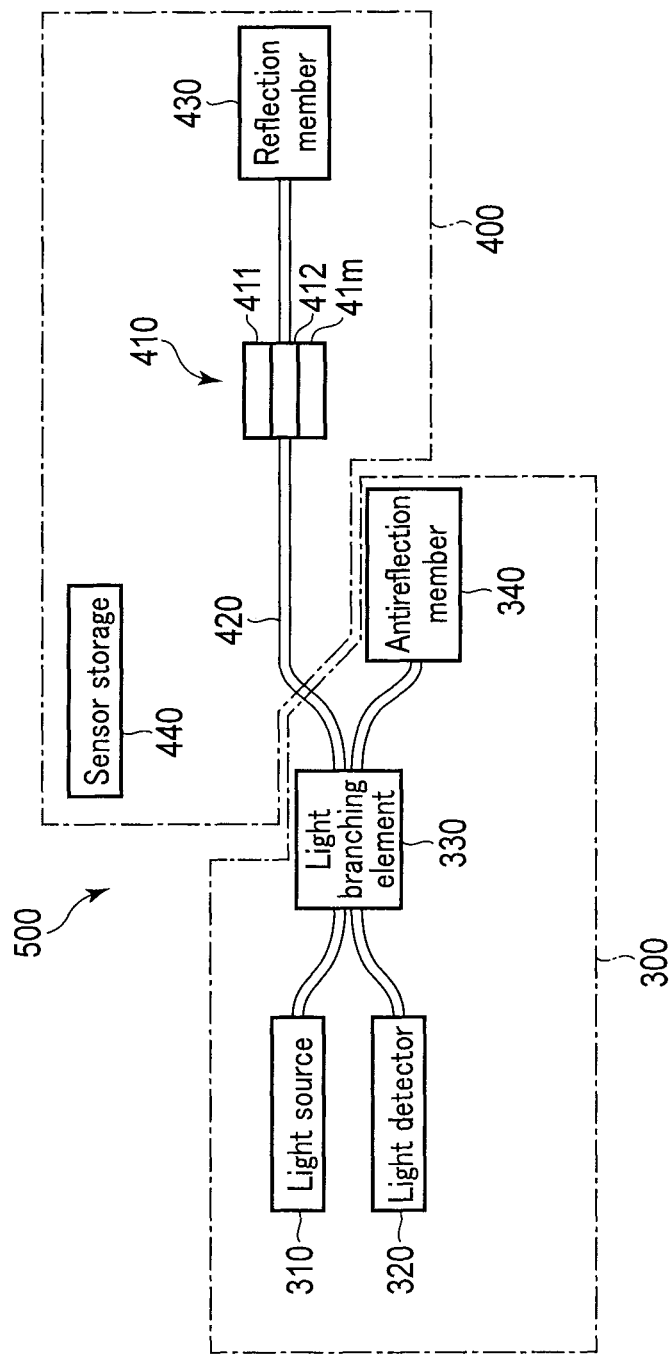
FIG. 19 is a block diagram showing an example of the configuration of the sensor.

FIG. 19 is a block diagram showing an example of the configuration of the sensor 500. In the present mode, the sensor assembly 400 includes a sensor storage 440. The sensor storage 440 prestores sensor identification information and bend coefficients, for example, at a time of factory shipment or at a time of device assembly. The sensor identification information, which is so-called ID information, is information for identifying the kind or the individual of the sensor assembly 400, and should preferably be unique. Also in the acquisition of the bend coefficients, the bend coefficients are stored in the sensor storage 440 in step S313 of FIG. 17. Thereby, even when the sensor assembly 400 is connected to a sensor driver, which is different from the sensor driver 300, the sensor identification information and bend coefficients can be read out from the sensor storage 440.

In addition, when a connection has been made to some other controller (when no bend coefficient exists in the storage 120), instead of acquiring the bend coefficients in step S3 of FIG. 16, the bend coefficients are read out of the sensor storage 440. Thereby, even when the sensor driver 300 has been connected to some other controller, it is not need to re-acquire the bend coefficients.

In an environment in which a plurality of sensors are used, a step in which the controller 100 confirms the sensor identification information of the connected sensor assembly 400 may be provided prior to step S2 immediately after the start of the flow of FIG. 15. In this case, it is presupposed that the bend coefficients and the sensor identification information are associated, and the bend coefficients (the bend coefficient of each of plural sensors) are stored in the storage 120.

In the step of confirming the sensor identification information, for example, the sensor identification information is input from the input unit 130 by the input device 190. The sensor identification information may be imprinted on or attached to the sensor assembly 400, or may be stored in a tag. Preferably, the tag is a non-contact tag such as an RF-ID. Alternatively, the sensor identification information may be stored in the above-described sensor storage 440 and read from it, or may be information stored in some other storage medium and read out. In addition, in the case of sensor identification information that fails to meet the above presupposition and is not stored in the storage 120, processes may be executed according to the flow of FIG. 15.

According to the second mode, since the bend coefficients can be extracted from the sensor identification information, even when a connection has been made to some other sensor, the bend coefficients can be extracted from the sensor identification information. Therefore, it is not need to re-acquire the bend coefficient.

(Third Mode)

Figure 20:
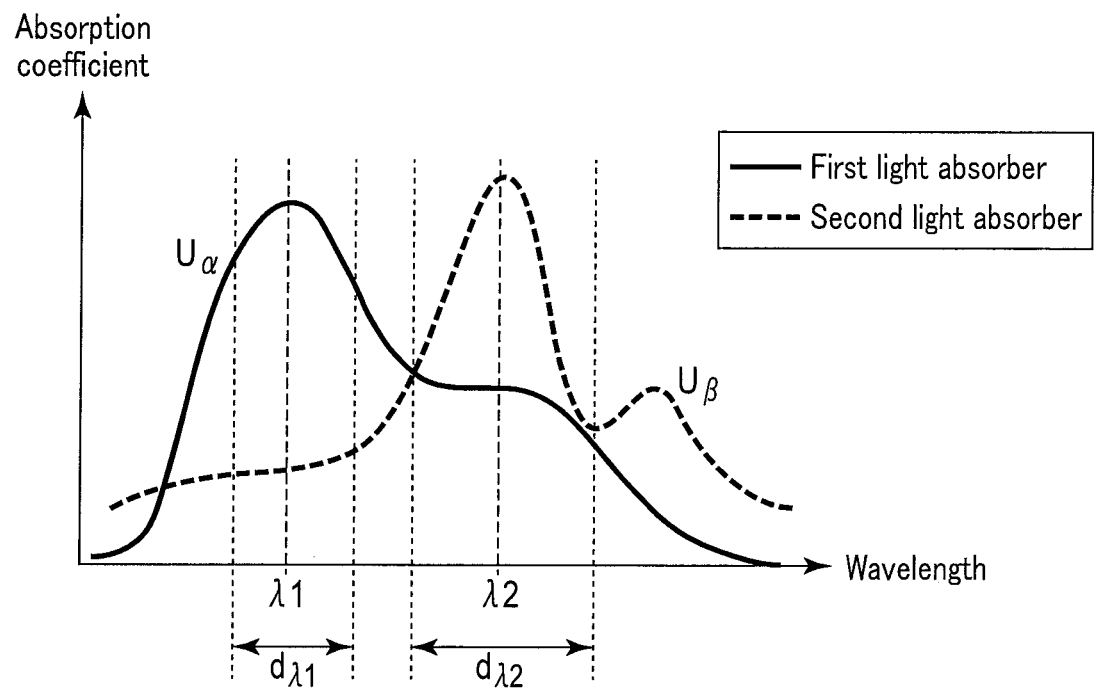
FIG. 20 is a graph showing an example of the relationship between the wavelength and the absorption coefficient of light in the first light absorber and the second light absorber.

FIG. 20 is a graph showing an example of the relationship between the wavelength and the absorption coefficient of light in the first light absorber and the second light absorber. The wavelengths to be used for the calculation of the bend information are not limited to specific wavelengths $\lambda 1$ and $\lambda 2$, and may be a first wavelength band $d_{\lambda 1}$ and a second wavelength band $d_{\lambda 2}$, each having a band width as shown in FIG. 20. For example, the first detection target 411 and the second detection target 412 include wavelength bands (characteristic absorption bands), and the wavelength band is a wavelength range of mutual absorption (that is, the wavelength range in which both the first light absorber and the second light absorber have absorption coefficients), and is a wavelength range of different absorption wavelength characteristics (that is, a wavelength range in which the first light absorber and the second light absorber differ in absorption coefficient from each other). The number of wavelength bands is equal to or larger than that of detection targets (that is, two or more).

In this case, for example, a mean value of light quantity information in a wavelength band of a target is used as the detected light quantity information.

According to the third mode, since the wavelengths that are used for the calculation of the bend information are each not a specific single wavelength, but each have a band width, it is not need to increase the wavelength resolution of the light detector 320. Accordingly, the cost of the light detector 320 can be reduced. In addition, since it is not that only local wavelengths are used, the robustness to noise is enhanced.

The wavelength bands to be used may include part of another wavelength band. For example, the first wavelength band and second wavelength band may overlap.

(Fourth Mode)

Figure 21:
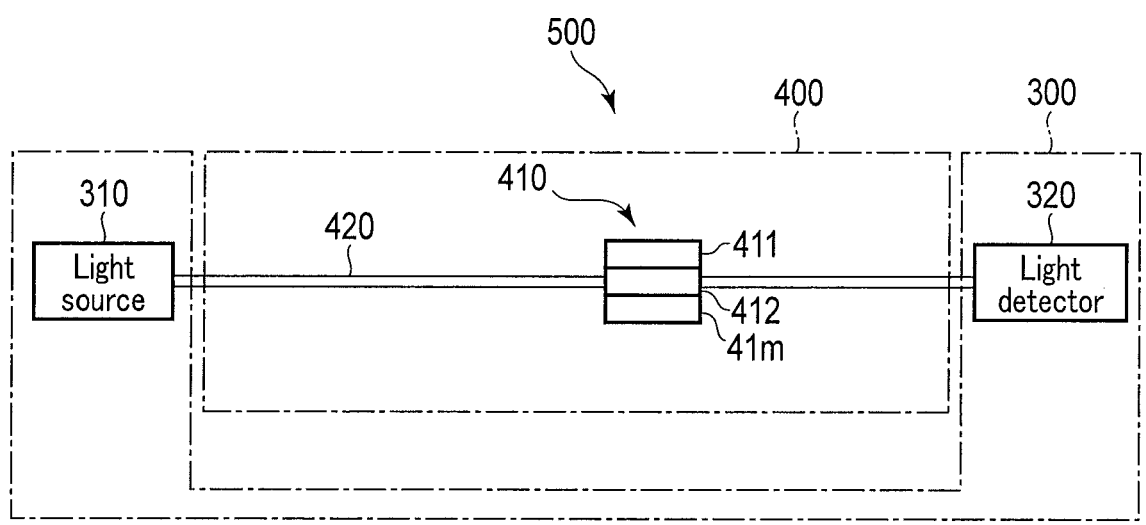
FIG. 21 is a block diagram showing an example of the configuration of the sensor.

FIG. 21 is a block diagram showing an example of the configuration of the sensor driver 300 and sensor assembly 400. The sensor driver 300 includes the light source 310 and the light detector 320. The sensor assembly 400 includes the light guide 420 provided with the detection target group 410. The above-described light branching element 330, antireflection member 340, and reflection member 430 are not provided. The light source 310 is optically connected to a base end of the light guide 420. The light detector 320 is optically connected to a tip end of the light guide 420. Light emitted from the light source 310 is guided to the light guide 420. The guided light transmits in the light guide 420 from the tip end side to the base end side, and reaches the light detector 320.

According to the mode in which the light branching element, antireflection member, and reflection member are not provided, since the loss of light due to these components can be decreased, the light quantity of the light source can be decreased.

(Fifth Mode)

The light detector 320 may be capable of detecting the detected light quantity information $D_{\lambda 1}$ and $D_{\lambda 2}$ at a plurality of predetermined wavelengths $\lambda 1$ and $\lambda 2$, or wavelength bands $d_{\lambda 1}$ and $d_{\lambda 2}$. For example, the wavelength characteristics of the emission intensity of light guided to the light guide 420 are varied at a time instant, and the light quantity at that time instant is detected.

FIG. 22 is a graph showing an example of the relationship between the wavelength and the light emission intensity of the light source at time instants t1 and t2 that are different from each other. In FIG. 22, the relationship at time instant t1 is indicated by a solid line, and the relationship at time instant t2 is indicated by a broken line. The light source 310 emits, by a filter or the like, light having a peak at wavelength $\lambda 1$ at time instant t1, and light having a peak at wavelength $\lambda 2$ at time instant t2. FIG. 23 is a graph showing an example of the relationship between the wavelength of light falling on the light detector and the detection sensitivity of the light detector, corresponding to FIG. 22. The light detector 320 includes a light receiving element (a light receiving element that does not have a spectral function by a filter or the like) having detection sensitivity to the intensity of light having peaks at the wavelengths $\lambda 1$ and $\lambda 2$.

According to the fifth mode, by detecting the light quantity from the light receiving element in synchronism with the time instants t1 and t2, the detected light quantity information (detection light quantity at each wavelength band) can be obtained.

The light emission of the light source 310 may be repeatedly executed. For example, the time instants t1 and t2 may be time instants corresponding to mutually different phases of a sine wave of time function. Specifically, the light source 310 may emit, at fixed cycles, light having a peak at the wavelength λ1 and light having a peak at the wavelength λ2.

Second Embodiment

A second embodiment of the present invention will be described with reference to FIG. 24 and FIG. 25. Hereinafter, a description of the parts common to the first embodiment is omitted, and only different parts are described.

Figure 24:
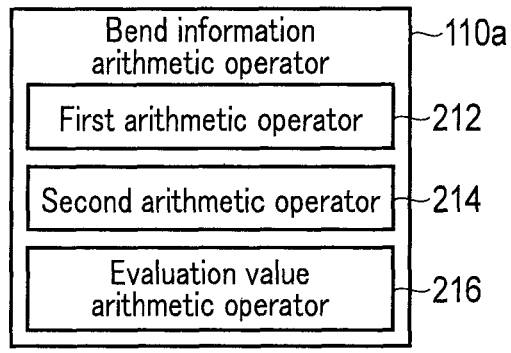
FIG. 24 is a block diagram showing an example of a bend information arithmetic operator in a second embodiment.
Figure 25:
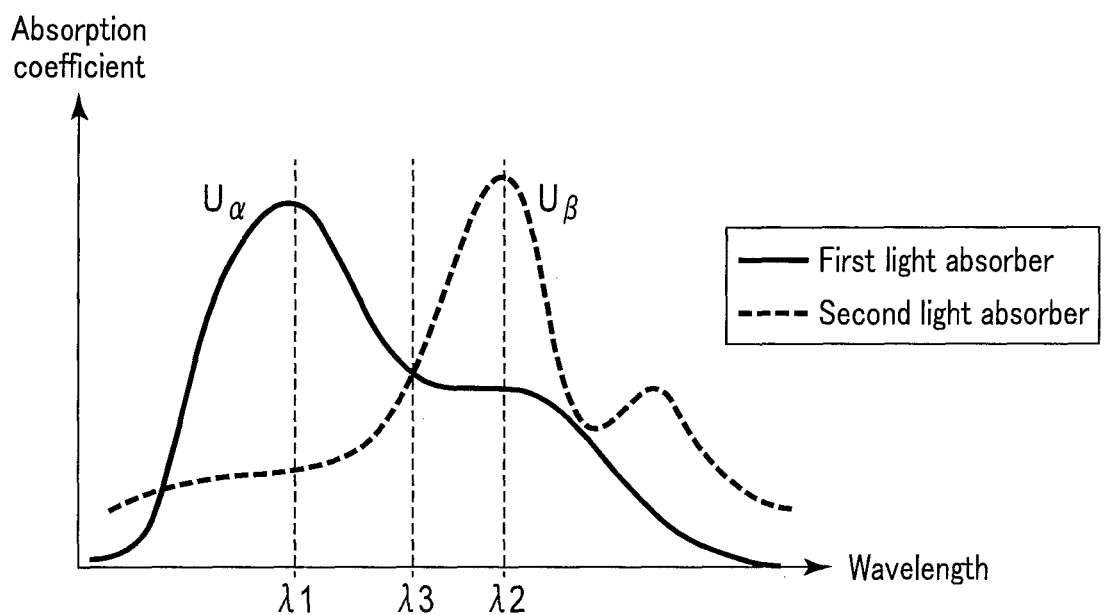
FIG. 25 is a graph showing an example of the relationship between the wavelength and the absorption coefficient of light in the first light absorber and the second light absorber.

FIG. 24 is a block diagram showing an example of a bend information arithmetic operator 110a in the second embodiment. The bend information arithmetic operator 110a includes the first arithmetic operator 212, the second arithmetic operator 214, and an evaluation value arithmetic operator 216 functioning as an optimizing arithmetic operator. The evaluation value arithmetic operator 216 executes an arithmetic operation for optimizing the bend information of the detection target group 410, as will be described below.

In the second embodiment, the bend information of the detection target group 410 is computed by utilizing the relationship between the wavelength and the absorption coefficient of light in the first light absorber and second light absorber, which is the same as in the first embodiment, and by using detected light quantity information $D_{\lambda 3}$, reference light quantity information $I_{\lambda 3}$, intensity modulation information $U_{\alpha \lambda 3}$, $U_{\beta \lambda 3}$, and a bend coefficient $\gamma(\theta, \kappa)$ of the detection target group 410 at a third wavelength λ3. FIG. 25 is a graph showing an example of the relationship between the wavelength and the absorption coefficient of light in the first light absorber and the second light absorber in the present embodiment. The third wavelength λ3 is a wavelength at which the absorption coefficient is different from the absorption coefficients at the first wavelength λ1 and second wavelength λ2.

In the present embodiment, in step S63 of the flow shown in FIG. 18, the evaluation value arithmetic operator 216 optimizes the bend coefficients of the detection target group 410 so that a difference between the right side and left side of each light quantity information relationship becomes minimum in the arithmetic operation by the first arithmetic operator 212.

Thus, to begin with, a difference $\Delta_{\lambda,n}$ between the right side and left side in equation (10) is calculated (n=1, 2, 3).

$$\Delta_{\lambda,n} = \ln[D_{\lambda,n}(\theta,\kappa)] - \ln(I_{\lambda,n}) - \alpha(\theta,\kappa) \cdot U_{\alpha\lambda,n} - \beta(\theta,\kappa) \cdot U_{\beta\lambda,n} \quad (12)$$

In order to optimize the bend coefficients, for example, an evaluation value J, which is the sum of square of difference $\Delta_{\lambda,n}$ at each wavelength, is calculated, and the bend coefficients of the detection target group 410 are determined so that the evaluation value J becomes minimum. The evaluation value J is given by the following equation (13).

$$J = \sum (\Delta_{\lambda n})^2 \quad (13)$$
$$= \Delta_{\lambda 1}^2 + \Delta_{\lambda 2}^2 + \Delta_{\lambda 3}^2$$

For example, as indicated by the following equation (14), the degree of contribution to the evaluation value J at each intensity modulation information may be adjusted by giving a weighting factor $w_n$.

$$J = \sum w_n (\Delta_{\lambda n})^2 \quad (14)$$
$$= w_1 \Delta_{\lambda 1}^2 + w_2 \Delta_{\lambda 2}^2 + w_3 \Delta_{\lambda 3}^2$$

In the setting of the weighting factor $w_n$, for example, it is better to increase the degree of contribution of such intensity modulation information that the light absorption quantities of the light absorbers of the detection target group 410 become maxima.

Furthermore, in step S64 of the flow shown in FIG. 18, the evaluation value arithmetic operator 216 optimizes the bend information of the detection target group 410 so that a difference between the right side and left side of each bend coefficient becomes minimum in the arithmetic operation by the second arithmetic operator 214. The method of optimization of the bend information is the same as the above-described method of optimization of the bend coefficients.

According to the present embodiment, the evaluation value arithmetic operator 216 executes the optimization arithmetic operation, so that the bend information of the detection target group 410 can be calculated with higher precision. In addition, it is possible to provide a bend information computation apparatus that has redundancy and is robust to an effect such as noise.

In addition, the optimization arithmetic operation can include a plurality of optimization arithmetic operations with mutually different convergences. For example, a first optimization arithmetic operation is a global optimization arithmetic operation, and has a high precision. A second optimization arithmetic operation is a local optimization arithmetic operation having a higher convergence than the first optimization arithmetic operation. The global optimization arithmetic operation is a method that can derive an optimal solution without falling into a local solution, such as particle swarm optimization (PSO), differential evolution (DE), a genetic algorithm (GA), and simulated annealing (SA). The local optimization arithmetic operation is a neighborhood search method to find a local solution, such as Newton's method, a steepest descent method, and a simplex method. The bend information computation apparatus can be configured to allow the user to select which of the arithmetic operations is to be executed, or whether a parallel operation of these arithmetic operations is to be executed. In this manner, the user can select the accuracy and the quickness of the arithmetic operation by himself/herself. For example, using the parallel operation of these arithmetic operations allows calculating an appropriate optimal solution quickly.

Third Embodiment

A third embodiment of the present invention will be described with reference to FIG. 26 to FIG. 30. Hereinafter, a description of the parts common to the first embodiment is omitted, and only different parts are described.

FIG. 26 is a block diagram showing an example of the configuration of the sensor 500, which is composed of the sensor driver 300 and the sensor assembly 400. In the third embodiment, the light guide 420 is provided with a first detection target group 410 including a first detection target 411 and a second detection target 412, and a second detection target group 450 including a third detection target 451 and a fourth detection target 452. The second detection target group 450 is disposed at a position different from that of the first detection target group 410 in the longitudinal direction of the light guide 420. The second detection target group 450 is formed like the first detection target group 410. The third detection target 451 is provided with a third light absorber, and the fourth detection target 452 is provided with a fourth light absorber. The positional relationship between the third detection target 451 and fourth detection target 452 is the same as the positional relationship between the first detection target 411 and second detection target 412.

Figure 27:
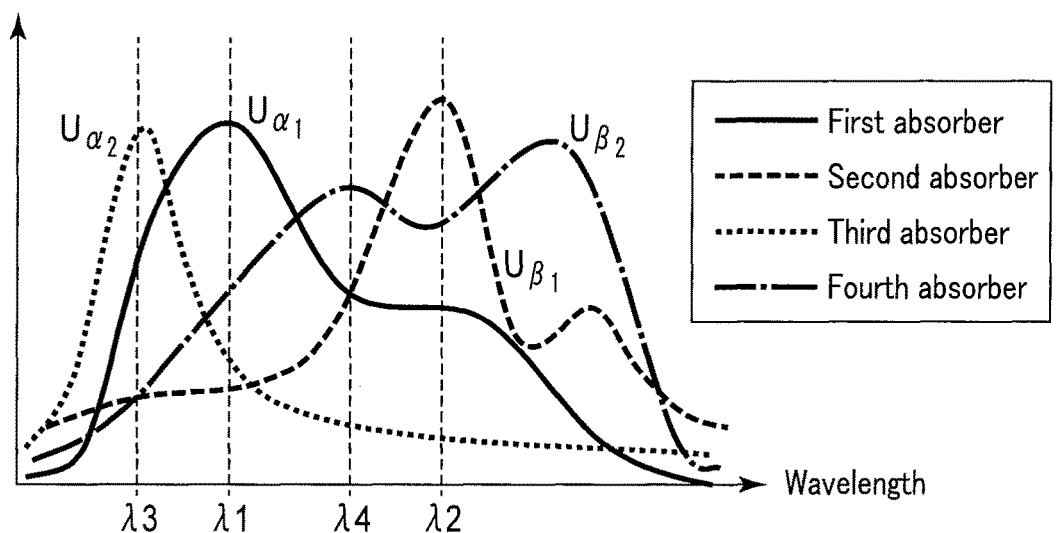
FIG. 27 is a graph showing an example of the relationship between the wavelength and the absorption coefficient of light in first, second, third, and fourth light absorbers.

FIG. 27 is a graph showing an example of the relationship between the wavelength and the absorption coefficient of light in the first, second, third, and fourth light absorbers. As shown in FIG. 27, the light absorbers provided in the different detection targets 411, 412, 451 and 452 have different light absorption coefficients at each of wavelengths $\lambda 1$, $\lambda 2$, $\lambda 3$, $\lambda 4$, that is, have mutually different absorption characteristics.

Figure 28A:
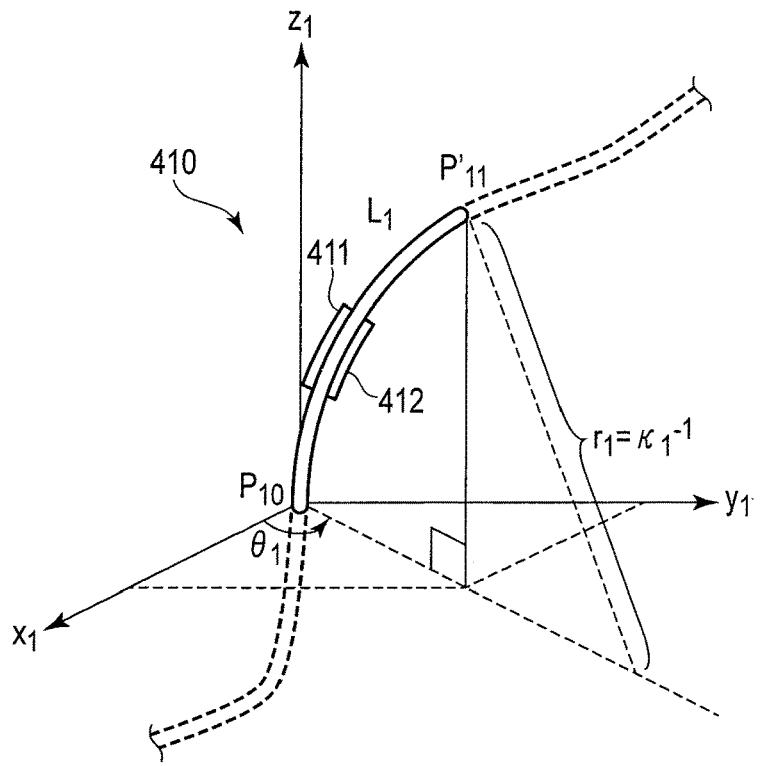
FIG. 28A is a view showing a state in which a region of the flexible portion having a length $L_1$ including a first detection target group is bent at an angle $\theta_1$ and a curvature $\kappa_1$.
Figure 28B:
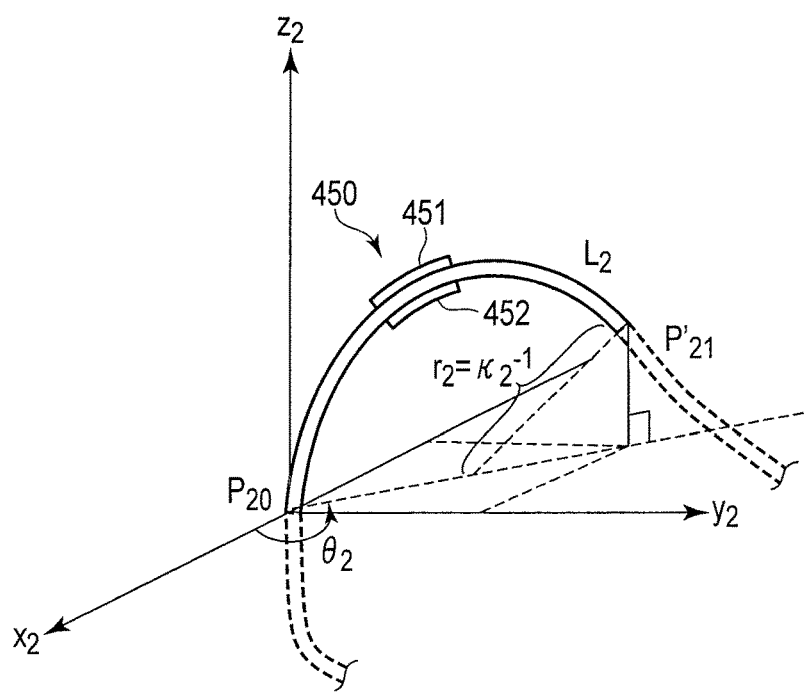
FIG. 28B is a view showing a state in which a region of the flexible portion having a length $L_2$ including a second detection target group is bent at an angle $\theta_2$ and a curvature $\kappa_2$.

Next, a description will be given of arithmetic operations that are executed in the arithmetic operator 101 of the computation apparatus 10 in order to compute bend information (angle $\theta_1$ and curvature $\kappa_1$) in the first detection target group 410 and bend information (angle $\theta_2$ and curvature $\kappa_2$) in the second detection target group 450. A state is now considered in which, of the flexible portion 819, a part with a length $L_1$ including the first detection target group 410 is bent at an angle $\theta_1$ and a curvature $\kappa_1$ shown in FIG. 28A, and a part with a length $L_2$ including the second detection target group 450 is bent at an angle $\theta_2$ and a curvature $\kappa_2$ shown in FIG. 28B. Incidentally, as shown in FIG. 28A and FIG. 28B, the angles $\theta_1$, $\theta_2$ are expressed by local coordinate systems (an $x_1 y_1 z_1$ coordinate system and an $x_2 y_2 z_2$ coordinate system) in the respective detection target groups 410 and 450. Accordingly, the direction of bend is expressed, for example, by the angle $\theta_1$ (FIG. 28A) formed between a straight line passing through a point $(x_1, y_1, 0)$, at which a point $P'_{11}(x_1, y_1, z_1)$ is projected onto an $x_1 y_1$ plane, and an origin $P_{10}(0, 0, 0)$, and an $x_1$ axis, and by the angle $\theta_2$ (FIG. 28B) formed between a straight line passing through a point $(x_2, y_2, 0)$, at which a point $P'_{21}(x_2, y_2, z_2)$ is projected onto an $x_2 y_2$ plane, and an origin $P_{20}(0, 0, 0)$, and an $x_2$ axis. In addition, the magnitude of bend is expressed by, for example, the curvature $\kappa_1$ and curvature $\kappa_2$.

Like equation (2), the detected light quantity $D_{\lambda n}$, which is detected by the light detector 320, is expressed as follows by using a product between the reference light quantity information $I_{\lambda n}$, variation ratios $F_{\lambda n}$ and $G_{\lambda n}$ in light quantity in the detection targets 411 and 412 of the first detection target group 410, and variation ratios $M_{\lambda n}$ and $N_{\lambda n}$ in light quantity in the detection targets 451 and 452 of the second detection target group 450.

$$D_{\lambda n} = I_{\lambda n} \times F_{\lambda n} \times G_{\lambda n} \times M_{\lambda n} \times N_{\lambda n} \tag{15}$$

Here $I_{\lambda n}$ is reference light quantity information, and is a light quantity about light of wavelength $\lambda n$, which is detected by the light detector 320 when both the first detection target group 410 and the second detection target group 450 are in the reference bend state. $F_{\lambda n}$ is a variation ratio in light quantity occurring due to light absorption by only the first detection target 411, and is a ratio between a light quantity about light of wavelength $\lambda n$ and the reference light quantity information $I_{\lambda n}$, the light quantity about light of wavelength $\lambda n$ being detected by the light detector 320 at a time when only the first detection target 411 of the first detection target group 410 is bent relative to the reference bend state. $G_{\lambda n}$ is a variation ratio in light quantity occurring due to light absorption by only the second detection target 412, and is a ratio between a light quantity about light of wavelength $\lambda n$ and the reference light quantity information $I_{\lambda n}$, the light quantity about light of wavelength $\lambda n$ being detected by the light detector 320 at a time when only the second detection target 412 of the first detection target group 410 is bent relative to the reference bend state. $M_{\lambda n}$ is a variation ratio in light quantity occurring due to light absorption by only the third detection target 451, and is a ratio between a light quantity about light of wavelength $\lambda n$ and the reference light quantity information $I_{\lambda n}$, the light quantity about light of wavelength $\lambda n$ being detected by the light detector 320 at a time when only the third detection target 451 of the second detection target group 450 is bent relative to the reference bend state. $N_{\lambda n}$ is a variation ratio in light quantity occurring due to light absorption by only the fourth detection target 452, and is a ratio between a light quantity about light of wavelength $\lambda n$ and the reference light quantity information $I_{\lambda n}$, the light quantity about light of wavelength $\lambda n$ being detected by the light detector 320 at a time when only the fourth detection target 452 of the second detection target group 450 is bent relative to the reference bend state.

Like the first embodiment, the variation ratios $F_{\lambda n}$, $G_{\lambda n}$, $M_{\lambda n}$, and $N_{\lambda n}$ are given by the following equations (16), (17), (18), and (19).

$$F_{\lambda n} = e^{\alpha_1(\theta_1, \kappa_1) \cdot U_{\alpha 1 \lambda n}} \tag{16}$$

$$G_{\lambda n} = e^{\beta_1(\theta_1, \kappa_1) \cdot U_{\beta 1 \lambda n}} \tag{17}$$

$$M_{\lambda n} = e^{\alpha_2(\theta_2, \kappa_2) \cdot U_{\alpha 2 \lambda n}} \tag{18}$$

$$N_{\lambda n} = e^{\beta_2(\theta_2, \kappa_2) \cdot U_{\beta 2 \lambda n}} \tag{19}$$

Here functions $\alpha_1(\theta_1, \kappa_1)$ and $\beta_1(\theta_1, \kappa_1)$ are, respectively, bend coefficients of the first detection target 411 and second detection target 412 of the first detection target group 410, and functions $\alpha_2(\theta_2, \kappa_2)$ and $\beta_2(\theta_2, \kappa_2)$ are, respectively, bend coefficients of the third detection target 451 and fourth detection target 452 of the second detection target group 450. $U_{\alpha 1 \lambda n}$ and $U_{\beta 1 \lambda n}$ are, respectively, pieces of intensity modulation information of the first detection target 411 and second detection target 412 of the detection target group 410, and $U_{\alpha 2 \lambda n}$ and $U_{\beta 2 \lambda n}$ are, respectively, pieces of intensity modulation information of the third detection target 451 and fourth detection target 452 of the detection target group 450. From equations (15), (16), (17), (18), and (19), the following equation (20) is obtained.

$$D_{\lambda n}(\theta_1, \kappa_1, \theta_2, \kappa_2) = \tag{20}$$
$$I_{\lambda n} \cdot e^{\alpha_1(\theta_1, \kappa_1) \cdot U_{\alpha 1 \lambda n}} \cdot e^{\beta_1(\theta_1, \kappa_1) \cdot U_{\beta 1 \lambda n}} \cdot e^{\alpha_2(\theta_2, \kappa_2) \cdot U_{\alpha 2 \lambda n}} \cdot e^{\beta_2(\theta_2, \kappa_2) \cdot U_{\beta 2 \lambda n}}$$

In equation (20), the left side expresses detected light quantity information in an arbitrary bend state, and the right side expresses a calculated light quantity value that is generated based on the reference light quantity information, bend coefficient and intensity modulation information. By taking a natural logarithm of both sides of equation (20), a light quantity information relationship expressed by the following equation (21) is obtained.

$$\ln[D_{\lambda,n}(\theta_1,\kappa_1,\theta_2,\kappa_2)]=\ln(I_{\lambda,n})+\alpha_1(\theta_1,\kappa_1)\cdot U_{\alpha_{1\lambda,n}}+\beta_1(\theta_1,\kappa_1)\cdot U_{\beta_{1\lambda,n}}+\alpha_2(\theta_2,\kappa_2)\cdot U_{\alpha_{2\lambda,n}}+\beta_2(\theta_2,\kappa_2)\cdot U_{\beta_{2\lambda,n}} \quad (21)$$

By taking the logarithm, the right side of equation (20) is expressed by addition. Thereby, equation (21) becomes easier to calculate, than equation (20).

As the reference bend state for determining the reference light quantity information $I_{\lambda,n}$, for example, the case in which both the detection target groups 410 and 450 are in the straight shape is adopted, that is, the case is adopted in which the curvature of the detection target group 410, 450 is 0, and the radius of curvature is ∞. For the purpose of convenience, it is assumed that the angles $\theta_1$ and $\theta_2$ of the detection target groups 410 and 450 are 0. The reference light quantity information $I_{\lambda,n}$ is given by the light quantity $D_{\lambda,n}(0, 0, 0, 0)$ at a time when the detection target groups 410, 450 are in the reference bend state. Specifically, the reference light quantity information $I_{\lambda,n}$ is given by the following equation (22).

$$I_{\lambda,n}=d_{\lambda,n}(0,0,0,0) \quad (22)$$

Figure 29:
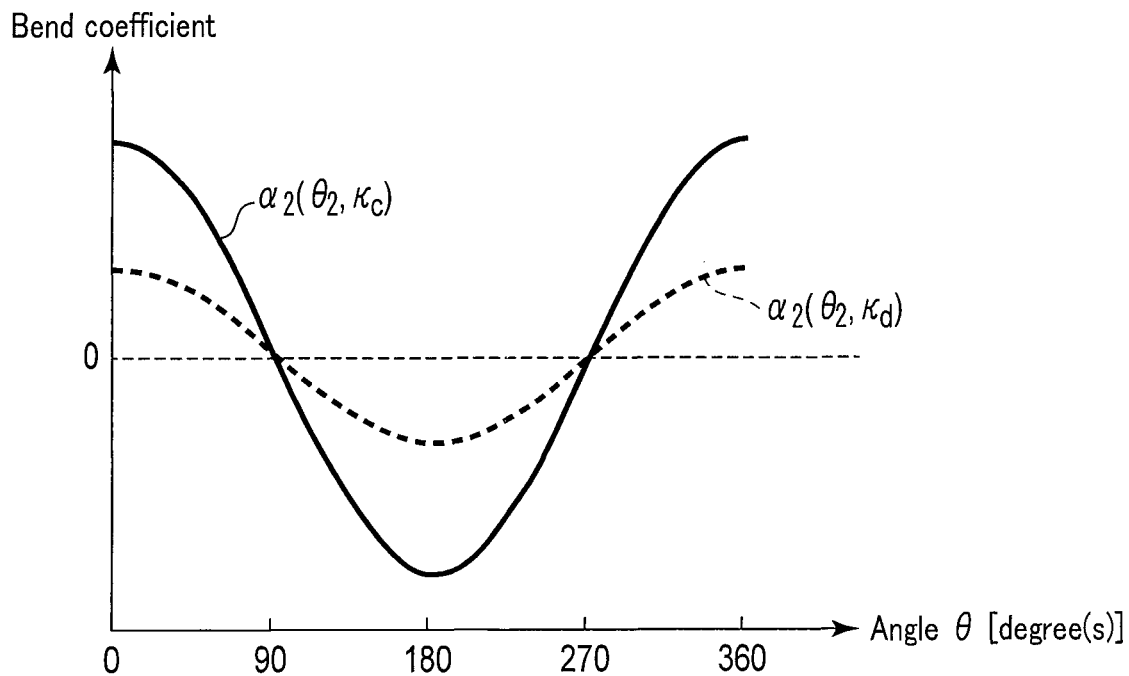
FIG. 29 is a graph showing an example of a bend coefficient obtained with respect to a first wavelength in connection with the second detection target group.
Figure 30:
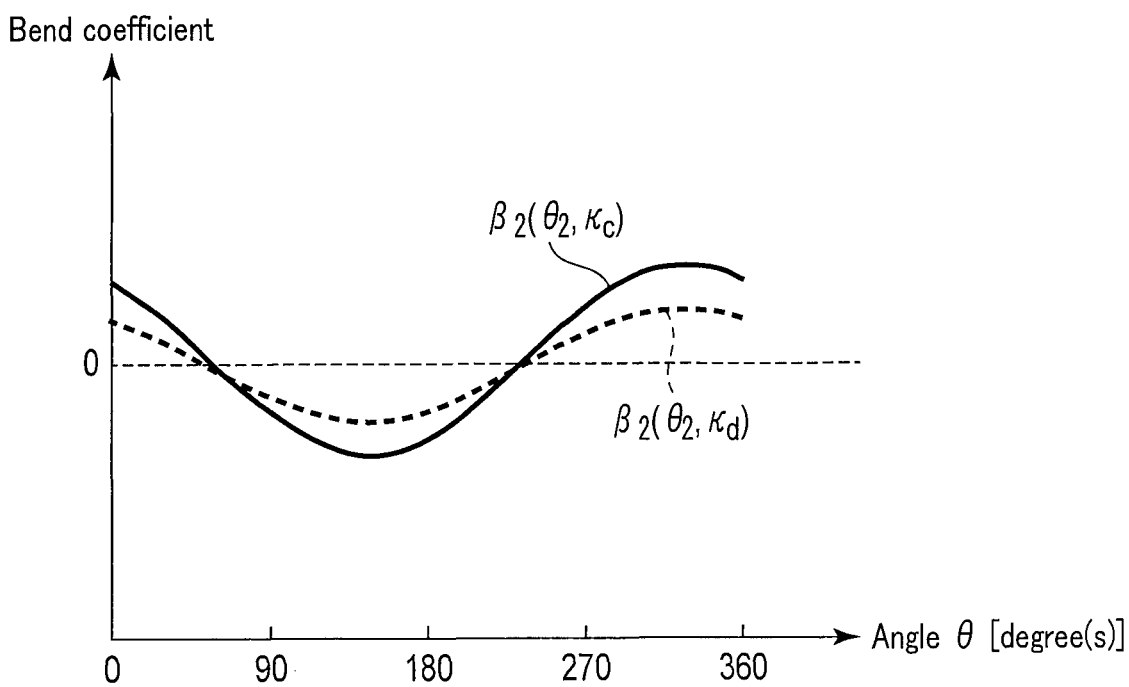
FIG. 30 is a graph showing an example of a bend coefficient obtained with respect to a second wavelength in connection with the second detection target group.

The bend coefficients $\alpha_1(\theta_1, \kappa_1)$ and $\beta_1(\theta_1, \kappa_1)$ are obtained by varying the angle $\theta_1$ and curvature $\kappa_1$ of the first detection target group 410 within possible ranges, while setting the second detection target group 450 in the reference bend state. In addition, the bend coefficients $\alpha_2(\theta_2, \kappa_2)$ and $\beta_2(\theta_2, \kappa_2)$ are obtained by varying the angle $\theta_2$ and curvature $\kappa_2$ of the detection target group 450 within possible ranges, while setting the first detection target group 410 in the reference bend state. The wavelengths that are used for arithmetic operations are wavelengths $\lambda 1$, $\lambda 2$, $\lambda 3$, and $\lambda 4$ of light respectively absorbed in the detection targets 411, 412, 451, and 452. The bend coefficients $\alpha_1(\theta_1, \kappa_1)$ and $\beta_1(\theta_1, \kappa_1)$ of the first detection target 411 and second detection target 412 of the first detection target group 410 are, for example, the same as shown in FIG. 11 and FIG. 12. FIG. 29 is a graph showing an example of the bend coefficient $\alpha_2(\theta_2, \kappa_2)$ obtained with respect to the third wavelength $\lambda 3$, that is, the bend coefficient $\alpha_2(\theta_2, \kappa_2)$ of the third detection target 451 of the second detection target group 450. FIG. 30 is a graph showing an example of the bend coefficient $\beta_2(\theta_2, \kappa_2)$ obtained with respect to the fourth wavelength $\lambda 4$, that is, the bend coefficient $\beta_2(\theta_2, \kappa_2)$ of the fourth detection target 452 of the second detection target group 450. In this manner, since the amplitude and phase differ depending on the wavelengths, the angle $\theta_2$ and curvature $\kappa_2$ are computable. FIG. 29 and FIG. 30 show, respectively, the bend coefficients with respect to two curvatures $\kappa_c$ and $\kappa_d$. Each of the bend coefficients $\alpha_1(\theta_1, \kappa_1)$, $\beta_1(\theta_1, \kappa_1)$, $\alpha_2(\theta_2, \kappa_2)$, and $\beta_2(\theta_2, \kappa_2)$ can be expressed by a periodic function. For example, these bend coefficients can be expressed approximately by sine functions of the following equations (23), (24), (25), and (26), respectively.

$$\alpha_1(\theta_1,\kappa_1)=a_{\alpha_1}(\kappa_1)\cdot\sin[\theta_1+b_{\alpha_1}(\kappa_1)]+c_{\alpha_1}(\kappa_1) \quad (23)$$

$$\beta_1(\theta_1,\kappa_1)=a_{\beta_1}(\kappa_1)\cdot\sin[\theta_1+b_{\beta_1}(\kappa_1)]+c_{\beta_1}(\kappa_1) \quad (24)$$

$$\alpha_2(\theta_2,\kappa_2)=a_{\alpha_2}(\kappa_2)\cdot\sin[\theta_2+b_{\alpha_2}(\kappa_2)]+c_{\alpha_2}(\kappa_2) \quad (25)$$

$$\beta_2(\theta_2,\kappa_2)=a_{\beta_2}(\kappa_2)\cdot\sin[\theta_2+b_{\beta_2}(\kappa_2)]+c_{\beta_2}(\kappa_2) \quad (26)$$

Here $a_{\alpha_1}(\kappa_1)$, $a_{\beta_1}(\kappa_1)$, $a_{\alpha_2}(\kappa_2)$, and $a_{\beta_2}(\kappa_2)$ are amplitudes, $b_{\alpha_1}(\kappa_1)$, $b_{\beta_1}(\kappa_1)$, $b_{\alpha_2}(\kappa_2)$, and $b_{\beta_2}(\kappa_2)$ are phases, and $c_{\alpha_1}(\kappa_1)$, $c_{\beta_1}(\kappa_1)$, $c_{\alpha_2}(\kappa_2)$, and $c_{\beta_2}(\kappa_2)$ are offsets.

In the present embodiment, the angles $\theta_1$ and $\theta_2$ and curvatures $\kappa_1$ and $\kappa_2$ in the first detection target group 410 and second detection target group 420 are calculated as follows.

To begin with, in the first arithmetic operator 212, based on the detected light quantity information $D_{\lambda 1}$, $D_{\lambda 2}$, $D_{\lambda 3}$ and $D_{\lambda 4}$ at the first, second, third, and fourth wavelengths $\lambda 1$, $\lambda 2$, $\lambda 3$, and $\lambda 4$ detected by the light detector 320, first-degree simultaneous equations with four variables expressed by the following equations (27) are solved with respect to $\alpha_1(\theta_1, \kappa_1)$, $\beta_1(\theta_1, \kappa_1)$, $\alpha_2(\theta_2, \kappa_2)$ and $\beta_2(\theta_2, \kappa_2)$ $$\begin{cases} \ln[D_{\lambda 1}(\theta_1,\kappa_1,\theta_2,\kappa_2)]-\ln(I_{\lambda 1})=\alpha_1(\theta_1,\kappa_1)\cdot U_{\alpha_{1\lambda 1}}+\beta_1(\theta_1,\kappa_1)\cdot U_{\beta_{1\lambda 1}}+\alpha_2(\theta_2,\kappa_2)\cdot U_{\alpha_{2\lambda 1}}+\beta_2(\theta_1,\kappa_1)\cdot U_{\beta_{2\lambda 1}} \\ \ln[D_{\lambda 2}(\theta_1,\kappa_1,\theta_2,\kappa_2)]-\ln(I_{\lambda 2})=\alpha_1(\theta_1,\kappa_1)\cdot U_{\alpha_{1\lambda 2}}+\beta_1(\theta_1,\kappa_1)\cdot U_{\beta_{1\lambda 2}}+\alpha_2(\theta_2,\kappa_2)\cdot U_{\alpha_{2\lambda 2}}+\beta_2(\theta_1,\kappa_1)\cdot U_{\beta_{2\lambda 2}} \\ \ln[D_{\lambda 3}(\theta_1,\kappa_1,\theta_2,\kappa_2)]-\ln(I_{\lambda 3})=\alpha_1(\theta_1,\kappa_1)\cdot U_{\alpha_{1\lambda 3}}+\beta_1(\theta_1,\kappa_1)\cdot U_{\beta_{1\lambda 3}}+\alpha_2(\theta_2,\kappa_2)\cdot U_{\alpha_{2\lambda 3}}+\beta_2(\theta_1,\kappa_1)\cdot U_{\beta_{2\lambda 3}} \\ \ln[D_{\lambda 4}(\theta_1,\kappa_1,\theta_2,\kappa_2)]-\ln(I_{\lambda 4})=\alpha_1(\theta_1,\kappa_1)\cdot U_{\alpha_{1\lambda 4}}+\beta_1(\theta_1,\kappa_1)\cdot U_{\beta_{1\lambda 4}}+\alpha_2(\theta_2,\kappa_2)\cdot U_{\alpha_{2\lambda 4}}+\beta_2(\theta_1,\kappa_1)\cdot U_{\beta_{2\lambda 4}} \end{cases} \quad (27)$$

The reference light quantity information $I_{\lambda 1}$, $I_{\lambda 2}$, $I_{\lambda 3}$, and $I_{\lambda 4}$ and intensity modulation information $U_{\alpha 1\lambda 1}$, $U_{\alpha 1\lambda 2}$, $U_{\alpha 1\lambda 3}$, $U_{\alpha 1\lambda 4}$, $U_{\beta 1\lambda 1}$, $U_{\beta 1\lambda 2}$, $U_{\beta 1\lambda 3}$, $U_{\beta 1\lambda 4}$, $U_{\alpha 2\lambda 1}$, $U_{\alpha 2\lambda 2}$, $U_{\alpha 2\lambda 3}$, $U_{\alpha 2\lambda 4}$, $U_{\beta 2\lambda 1}$, $U_{\beta 2\lambda 2}$, $U_{\beta 2\lambda 3}$, and $U_{\beta 2\lambda 4}$ are obtained in advance and stored in the storage 120. Accordingly, in the first arithmetic operator 212, the light quantity variation information $\alpha_1$, $\beta_1$, $\alpha_2$, and $\beta_2$ in the detection targets 411, 412, 451, and 452 can be calculated.

Next, in the second arithmetic operator 214, simultaneous equations with two variables expressed by the following equations (28) obtained according to the light quantity variation information $\alpha_1$ and $\beta_1$ calculated by the first arithmetic operator 212 and the bend coefficients $\alpha_1(\theta_1, \kappa_1)$ and $\beta_1(\theta_1, \kappa_1)$ stored in the storage 120 are solved with respect to $\theta_1$ and $\kappa_1$.

$$\begin{cases} \alpha_1(\theta_1,\kappa_1)=a_{\alpha_1}(\kappa_1)\cdot\sin[\theta_1+b_{\alpha_1}(\kappa_1)]+c_{\alpha_1}(\kappa_1) \\ \beta_1(\theta_1,\kappa_1)=a_{\beta_1}(\kappa_1)\cdot\sin[\theta_1+b_{\beta_1}(\kappa_1)]+c_{\beta_1}(\kappa_1) \end{cases} \quad (28)$$

Furthermore, in the second arithmetic operator 214, simultaneous equations with two variables expressed by the following equations (29) obtained according to the light quantity variation information $\alpha_2$ and $\beta_2$ calculated by the first arithmetic operator 212 and the bend coefficients $\alpha_2(\theta_2, \kappa_2)$ and $\beta_2(\theta_2, \kappa_2)$ stored in the storage 120 are solved with respect to $\theta_2$ and $\kappa_2$.

$$\begin{cases} \alpha_2(\theta_2,\kappa_2)=a_{\alpha_2}(\kappa_2)\cdot\sin[\theta_2+b_{\alpha_2}(\kappa_2)]+c_{\alpha_2}(\kappa_2) \\ \beta_2(\theta_2,\kappa_2)=a_{\beta_2}(\kappa_2)\cdot\sin[\theta_2+b_{\beta_2}(\kappa_2)]+c_{\beta_2}(\kappa_2) \end{cases} \quad (29)$$

In this manner, the angle $\theta_1$ and curvature $\kappa_1$, that is, the bend information, in the detection target group 410, and the angle $\theta_2$ and curvature $\kappa_2$, that is, the bend information, in the detection target group 450, can be calculated.

The present embodiment has the configuration in which the two detection target groups 410 and 450 are provided on the light guide 420 at different positions in the longitudinal direction of the light guide 420. However, the embodiment may be modified to have such a configuration that a greater number of detection target groups 410 are provided on the light guide 420, as shown in FIG. 31.

In this case, too, the bend information of each detection target group 410 can be calculated by the same manner. Specifically, the bend information is calculated in the following manner. Here, it is assumed that the number of detection target groups 410 is m. In addition, it is assumed that a natural number of 1 to m is n (i.e. n=1, 2, . . . , m).

Bend coefficients $\alpha_n(\theta_n, \kappa_n)$ and $\beta_n(\theta_n, \kappa_n)$ of a (2n−1)th detection target and a (2n)th detection target of an n-th detection target group are obtained by varying an angle $\theta_n$ and a curvature $\kappa_n$ of the n-th detection target group within possible ranges, while setting the detection target groups other than the n-th detection target group in the reference bend state.

The bend information arithmetic operation is executed in the following manner.

To begin with, first-degree simultaneous equations with 2m variables expressed by the following equations (30) are solved with respect to $a_n(\theta_n, \kappa_n)$ and $\beta_n(\theta_n, \kappa_n)$.

$$\begin{cases} \ln[D_{\lambda 1}(\theta_1, \kappa_1, \ldots, \theta_m, \kappa_m)] - \ln(I_{\lambda 1}) = \\ \alpha_1(\theta_1, \kappa_1) \cdot U_{\alpha_{1_{\lambda 1}}} + \beta_1(\theta_1, \kappa_1) \cdot U_{\beta_{1_{\lambda 1}}} + \ldots + \\ \alpha_m(\theta_m, \kappa_m) \cdot U_{\alpha_{m_{\lambda 1}}} + \beta_m(\theta_m, \kappa_m) \cdot U_{\beta_{m_{\lambda 1}}} \\ \ln[D_{\lambda 2}(\theta_1, \kappa_1, \ldots, \theta_m, \kappa_m)] - \ln(I_{\lambda 2}) = \\ \alpha_1(\theta_1, \kappa_1) \cdot U_{\alpha_{1_{\lambda 2}}} + \beta_1(\theta_1, \kappa_1) \cdot U_{\beta_{1_{\lambda 2}}} + \ldots + \\ \alpha_m(\theta_m, \kappa_m) \cdot U_{\alpha_{m_{\lambda 2}}} + \beta_m(\theta_m, \kappa_m) \cdot U_{\beta_{m_{\lambda 2}}} \\ \vdots \\ \ln[D_{\lambda 2m}(\theta_1, \kappa_1, \ldots, \theta_m, \kappa_m)] - \ln(I_{\lambda 2m}) = \\ \alpha_1(\theta_1, \kappa_1) \cdot U_{\alpha_{1_{\lambda 2m}}} + \beta_1(\theta_1, \kappa_1) \cdot U_{\beta_{1_{\lambda 2m}}} + \ldots + \\ \alpha_m(\theta_m, \kappa_m) \cdot U_{\alpha_{m_{\lambda 2m}}} + \beta_m(\theta_m, \kappa_m) \cdot U_{\beta_{m_{\lambda 2m}}} \end{cases} \quad (30)$$

Next, an m-number of sets of simultaneous equations with two variables expressed by the following equations (31) are solved with respect to $\theta_n$ and $\kappa_n$.

$$\begin{cases} \alpha_1(\theta_1, \kappa_1) = a_{\alpha_1}(\kappa_1) \cdot \sin[\theta_1 + b_{\alpha_1}(\kappa_1)] + c_{\alpha_1}(\kappa_1) \\ \beta_1(\theta_1, \kappa_1) = a_{\beta_1}(\kappa_1) \cdot \sin[\theta_1 + b_{\beta_1}(\kappa_1)] + c_{\beta_1}(\kappa_1) \end{cases} \quad (31)$$

$$\begin{cases} \alpha_2(\theta_2, \kappa_2) = a_{\alpha_2}(\kappa_2) \cdot \sin[\theta_2 + b_{\alpha_2}(\kappa_2)] + c_{\alpha_2}(\kappa_2) \\ \beta_2(\theta_2, \kappa_2) = a_{\beta_2}(\kappa_2) \cdot \sin[\theta_2 + b_{\beta_2}(\kappa_2)] + c_{\beta_2}(\kappa_2) \end{cases}$$

$$\vdots$$

$$\begin{cases} \alpha_m(\theta_m, \kappa_m) = a_{\alpha_m}(\kappa_m) \cdot \sin[\theta_m + b_{\alpha_m}(\kappa_m)] + c_{\alpha_m}(\kappa_m) \\ \beta_m(\theta_m, \kappa_m) = a_{\beta_m}(\kappa_m) \cdot \sin[\theta_m + b_{\beta_m}(\kappa_m)] + c_{\beta_m}(\kappa_m) \end{cases}$$

Thereby, the bend information ($\theta_n$, $\kappa_n$) of each detection target group 410 is calculated.

[Modification]

FIG. 32A and FIG. 32B show another detection target 461 alternative to the detection targets 411, 412, . . . , 41m, 451, and 452. FIG. 32A is a cross-sectional view in a radial direction of the light guide 420 at a location where the detection target 461 is provided. FIG. 32B is a cross-sectional view including an optical axis of the light guide 420 at the location where the detection target 461 is provided.

The detection target 461 is what is formed, at a desired position in the longitudinal axial direction of the optical fiber, by removing the jacket 421 and clad 422 to expose a part of the core 423, and then holographically forming a grating 426, which is an optical characteristic changing member, with a photopolymer on the exposed part of the core 423. Incidentally, the jacket 421 and clad 422 are removed by using a laser process, or a photo process and an etching process. At this time, if micro damage is caused to the core 423, light would leak, guided light would be lost, or the core 423 would become less robust to bending. Thus, it is desirable to perform processing by a method that does not damage the core 423 as much as possible.

In this manner, the detection target 461 is formed such that the grating 426 is put in contact with the core 423. Alternatively, as shown in FIG. 33, the grating 426 may be formed in a part of the clad 422, without being in contact with the core 423.

The grating 426 causes a diffraction phenomenon when light propagates through the inside or is reflected at the surface, thereby transmitting, while intensifying, light of a specific wavelength traveling in a predetermining direction different from the direction of incidence of light to the grating 426. In FIG. 32B, measurement light is indicated by solid-line arrows, and the light of the specific wavelength, which is caused to travel in the predetermined direction by the grating 426, is indicated by broken-line arrows.

The endoscope has been taken as an example of the device to which the bend information computation apparatus is applied, and the endoscope system has been described. However, the object into which the bend information computation apparatus is incorporated is not limited to the endoscope, and the bend information computation apparatus is applicable to a catheter, which is inserted into an insertion target, a surgery-assisting robot, etc.

The present invention is not limited to the foregoing embodiment described above, but it is evident to a person with ordinary skill in the art that various improvements and modifications can be made without departing from the subject matter of the present invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A bend information computation apparatus to compute bend information representing a direction of bend and a magnitude of bend of a detection target group provided on a light guide, the detection target group including a plurality of detection targets disposed at an identical position along a length of the light guide, and each of the detection targets modulating the intensity of light guided by the light guide in accordance with the direction of bend and the magnitude of bend, the bend information computation apparatus comprising:

a controller comprising hardware, the controller being configured to:
receive detected light quantity information of light of a wavelength corresponding to each of the detection targets;
store a bend coefficient and intensity modulation information of each of the detection targets, and a light quantity information relationship representing a relationship between the bend coefficient and intensity modulation information and the detected light quantity information;

calculate light quantity variation information of each of the detection targets, based on the detected light quantity information and the light quantity information relationship; and calculate the bend information of the detection target group, based on the light quantity variation information and the bend coefficient;

wherein the bend coefficient is a bend coefficient that varies in accordance with the bend information of the detection target group; and the bend coefficient is expressed by a periodic function of a curvature and the direction of bend in the detection target group.

2. The bend information computation apparatus of claim 1, wherein the periodic function is expressed by a sine function.

3. The bend information computation apparatus of claim 1, wherein the light quantity information relationship includes reference light quantity information, and the reference light quantity information is the detected light quantity information acquired in a state in which the detection target group is set in a predetermined reference bend state.

4. The bend information computation apparatus of claim 3, wherein the predetermined reference bend state is a state in which the detection target group is set in a straight shape.

5. The bend information computation apparatus of claim 1, wherein the intensity modulation information is a relationship between an absorption degree and a wavelength of light in the detection target.

6. A bend information computation apparatus to compute bend information representing a direction of bend and a magnitude of bend of a detection target group provided on a light guide, the detection target group including a plurality of detection targets disposed at an identical position along a length of the light guide, and each of the detection targets modulating the intensity of light guided by the light guide in accordance with the direction of bend and the magnitude of bend, the bend information computation apparatus comprising:

a controller comprising hardware, the controller being configured to:

receive detected light quantity information of light of a wavelength corresponding to each of the detection targets;

store a bend coefficient and intensity modulation information of each of the detection targets, and a light quantity information relationship representing a relationship between the bend coefficient and intensity modulation information and the detected light quantity information;

calculate light quantity variation information of each of the detection targets, based on the detected light quantity information and the light quantity information relationship; and calculate the bend information of the detection target group, based on the light quantity variation information and the bend coefficient;

wherein the calculating of the light quantity variation information of each of the detection targets and the calculating of the bend information of the detection target group include calculating the bend information of the detection target by an optimization arithmetic operation, and the optimization arithmetic operation optimizes the bend coefficient so that a difference between a right side and a left side of an equation of the light quantity information relationship becomes minimum in an arithmetic operation in the calculating of the light quantity variation information of each of the detection targets, and optimizes the bend coefficient so that a difference between a right side and a left side of an equation of the bend coefficient becomes minimum in an arithmetic operation in the calculating of the bend information of the detection target group.

7. The bend information computation apparatus of claim 1, further comprising a sensor to acquire the detected light quantity information, the sensor comprising:

a light source;

the light guide to guide light emitted from the light source;

the plurality of detection targets including optical members with mutually different light modulation characteristics; and a light sensor for detecting light quantity of light that is guided by the light guide at each of a plurality of wavelength bands and outputting the detected light quantity information to the controller.

8. An endoscope system comprising:

the bend information computation apparatus of claim 7;

an endoscope provided with the light guide in an insertion portion; and an endoscope bend information calculator to calculate bend information of the insertion portion, based on the bend information of the detection target group.

9. A bend information computation method to compute bend information representing a direction of bend and a magnitude of bend of a detection target group provided on a light guide, the detection target group including a plurality of detection targets disposed at an identical position along a length of the light guide, and each of the detection targets modulating the intensity of light guided by the light guide in accordance with the direction of bend and the magnitude of bend, the bend information computation method comprising:

acquiring detected light quantity information of light of a wavelength corresponding to each of the detection targets;

acquiring a bend coefficient and intensity modulation information of each of the detection targets, and a light quantity information relationship representing a relationship between the bend coefficient and intensity modulation information and the detected light quantity information;

calculating light quantity variation information of each of the detection targets, based on the detected light quantity information and the light quantity information relationship; and calculating the bend information of the detection target group, based on the light quantity variation information and the bend coefficient;

wherein the bend coefficient is a bend coefficient that varies in accordance with the bend information of the detection target group; and the bend coefficient is expressed by a periodic function of a curvature and the direction of bend in the detection target group.

10. A program for bend information computation to compute bend information representing a direction of bend and a magnitude of bend of a detection target group provided on a light guide, the detection target group including a plurality of detection targets disposed at an identical position along a length of the light guide, and each of the detection targets modulating the intensity of light guided by the light guide in accordance with the direction of bend and the magnitude of bend, the program causing a computer to execute:
- acquiring detected light quantity information of light of a wavelength corresponding to each of the detection targets;
- acquiring a bend coefficient and intensity modulation information of each of the detection targets, and a light quantity information relationship representing a relationship between the bend coefficient and intensity modulation information and the detected light quantity information;
- calculating light quantity variation information of each of the detection targets, based on the detected light quantity information and the light quantity information relationship; and
- calculating the bend information of the detection target group, based on the light quantity variation information and the bend coefficient;
- wherein the bend coefficient is a bend coefficient that varies in accordance with the bend information of the detection target group; and
- the bend coefficient is expressed by a periodic function of a curvature and the direction of bend in the detection target group.

* * * * *